Figure 2:
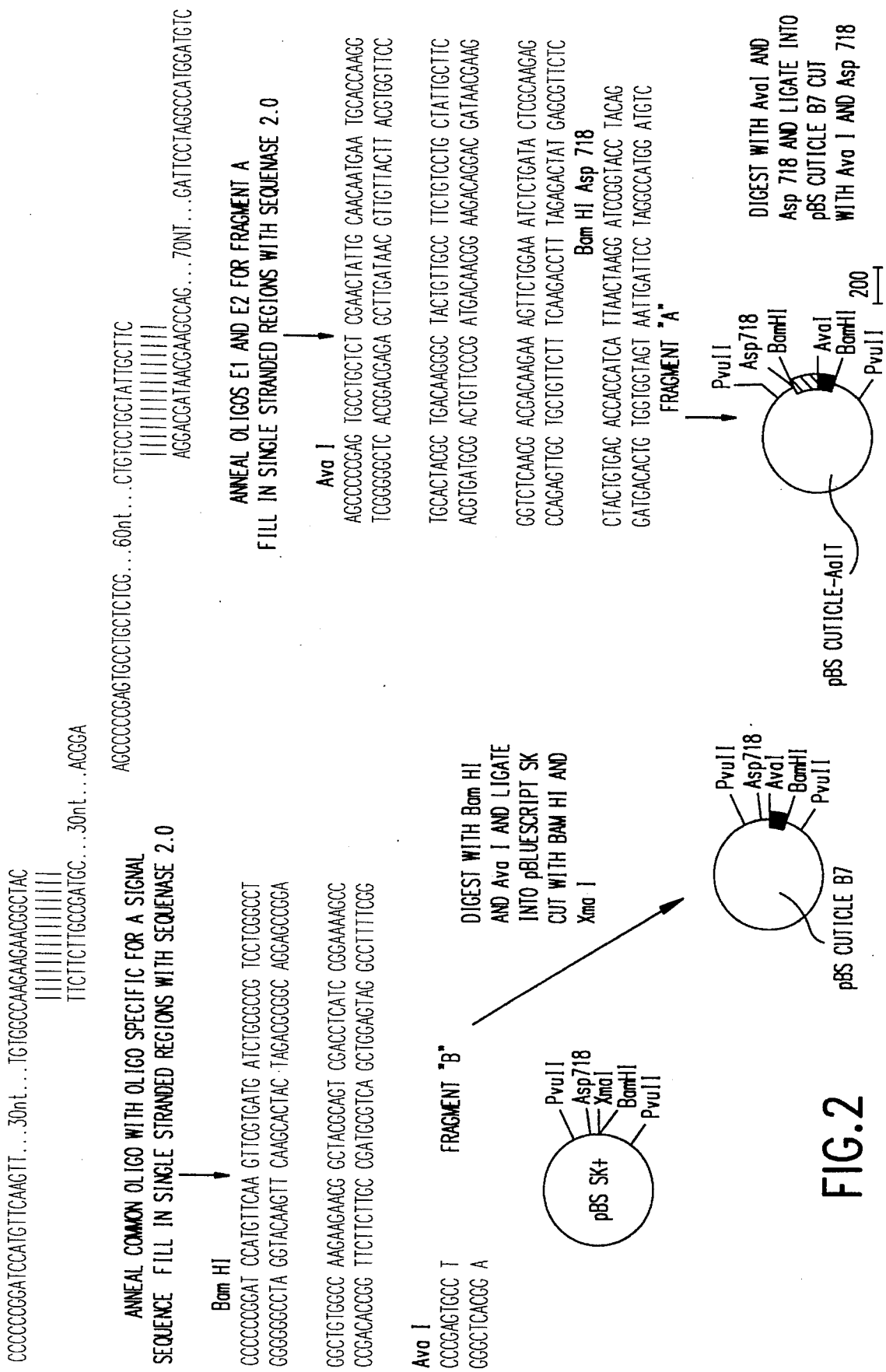

United States Patent [19]

Black et al.

[11] Patent Number: 5,547,871

[45] Date of Patent: Aug. 20, 1996

[54] HETEROLOGOUS SIGNAL SEQUENCES FOR SECRETION OF INSECT CONTROLLING PROTEINS

[75] Inventors: Bruce C. Black, Yardley, Pa.; Max D. Summers, Bryan, Tex.

[73] Assignee: American Cyanamid Company, Wayne, N.J.

[21] Appl. No.: 9,265

[22] Filed: Jan. 25, 1993

(Under 37 CFR 1.47)

[51] Int. Cl.$^6$ .............................. C12N 7/01; C12N 15/32; C12N 15/85

[52] U.S. Cl. .................. 435/240.1; 435/69.8; 435/320.1; 935/48; 935/13; 935/14; 536/23.2; 536/23.51; 536/23.71; 536/23.4

[58] Field of Search ................................. 536/23.1–23.51, 536/23.7, 23.72, 24.1; 935/48, 13, 14; 435/69.8, 240.1, 252.3, 320.1; 530/350

[56] References Cited

U.S. PATENT DOCUMENTS 5,155,037  10/1992  Summers ............................. 435/240.2
5,266,317  11/1993  Tomalski et al. ...................... 424/93 T

FOREIGN PATENT DOCUMENTS 0431829  6/1991  European Pat. Off. .
0505207  9/1992  European Pat. Off. .

OTHER PUBLICATIONS

Bougis et al., *J. Biol. Chem.*, vol. 264, No. 32, Nov. 15, 1989, pp. 19259–19265.

*Primary Examiner*—Robert A. Wax
*Assistant Examiner*—Keith D. Hendricks
*Attorney, Agent, or Firm*—Darryl L. Webster; Alan M. Gordon

[57] ABSTRACT

Seven heterologous signal sequence are described for use with genes for insect controlling proteins, such that when the signal sequence and protein genes are inserted into an insect virus, that virus demonstrates an earlier onset of morbidity than a wild-type insect virus which lacks the gene for the insect controlling protein.

21 Claims, 16 Drawing Sheets

```
NAT.  AAG AAG AAT GGA TAT GCC GTC GAT AGT AGT GGT AAA GCT CCT GAA
C.O.  .........C...C...C...A.......C.TCA.TCC...A.......C...C...G
      lys lys asn gly tyr ala val asp ser ser gly lys ala pro glu NAT.  TGT CTT TTG AGC AAT TAC TGT AAC AAC GAA TGC ACA AAA GTA CAT
C.O.  ..C...G.C.C.TCG...C...T...C.......T..........C...G...G...C
      cys leu leu ser asn tyr cys asn asn glu cys thr lys val his NAT.  TAT GCT GAC AAA GGA TAT TGC TGC TTA CTT TCA TGT TAT TGC
C.O.  ..C...........G...C...C...T.....C.T...G...C...C........
      tyr ala asp lys gly try cys cys leu leu ser cys tyr cys NAT.  TTC GGT CTA AAT GAC GAT AAA AAA GTT TTG GAG ATT TCG GAC ACA
C.O.  .........C...C.......C...G.........C.....A...C...T...T...T
      phe gly leu asn asp asp lys lys val leu glu ile ser asp thr NAT.  AGG AAA AGT TAT TGT GAC ACC ACA ATA ATT AAT TAA
C.O.  C.C...G...C...C..............C...C.......C....
      arg lys ser tyr cys asp thr thr ile ile asn . . .
```

FIG. 1

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bombyx mori ( i x ) FEATURE:
        ( A ) NAME/KEY: CDS
        ( B ) LOCATION: 13..60

( x i ) SEQUENCE DESCRIPTION: SEQ ID NO:1:

```
CCCCCCGGAT CC ATG AAA CTC CTG GTC GTG TTC GCC ATG TGC GTG CCC       48
              Met Lys Leu Leu Val Val Phe Ala Met Cys Val Pro
               1           5                  10

GCT GCC AGC GCT                                                    60
Ala Ala Ser Ala
         15
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Leu Leu Val Val Phe Ala Met Cys Val Pro Ala Ala Ser Ala
 1               5                  10                      15
```

( 2 ) INFORMATION FOR SEQ ID NO:3:

( i ) SEQUENCE CHARACTERISTICS:
   ( A ) LENGTH: 59 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
   ( A ) ORGANISM: Bombyx mori ( i x ) FEATURE:
   ( A ) NAME/KEY: CDS
   ( B ) LOCATION: 12..59

( x i ) SEQUENCE DESCRIPTION: SEQ ID NO:3:

```
CTCCTAACAA A ATG AAA CTT CTC GTT GTG TTC GCA ATG TGC GTG CCT GCC      50
            Met Lys Leu Leu Val Val Phe Ala Met Cys Val Pro Ala
             1           5                   10

GCC AGC GCC                                                           59
Ala Ser Ala
     15
```

( 2 ) INFORMATION FOR SEQ ID NO:4:

( i ) SEQUENCE CHARACTERISTICS:
       ( A ) LENGTH: 16 amino acids
       ( B ) TYPE: amino acid
       ( D ) TOPOLOGY: linear ( i i ) MOLECULE TYPE: protein ( x i ) SEQUENCE DESCRIPTION: SEQ ID NO:4:

```
Met Lys Leu Leu Val Val Phe Ala Met Cys Val Pro Ala Ala Ser Ala
 1               5                   10                  15
```

( 2 ) INFORMATION FOR SEQ ID NO:5:

( i ) SEQUENCE CHARACTERISTICS:
       ( A ) LENGTH: 69 base pairs
       ( B ) TYPE: nucleic acid
       ( C ) STRANDEDNESS: single
       ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
       ( A ) ORGANISM: Manduca sexta ( i x ) FEATURE:
       ( A ) NAME/KEY: CDS
       ( B ) LOCATION: 13..69

( x i ) SEQUENCE DESCRIPTION: SEQ ID NO:5:

```
CCCCCCGGAT CC ATG TAC AAA CTG ACC GTC TTC CTG ATG TTC ATC GCC         48
              Met Tyr Lys Leu Thr Val Phe Leu Met Phe Ile Ala
               1           5                   10

TTC GTG ATT ATC GCT GAG GCC                                           69
Phe Val Ile Ile Ala Glu Ala
             15
```

( 2 ) INFORMATION FOR SEQ ID NO:6:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

Met Tyr Lys Leu Thr Val Phe Leu Met Phe Ile Ala Phe Val Ile Ile
 1               5                  10                  15
Ala Glu Ala ( 2 ) INFORMATION FOR SEQ ID NO:7:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Manduca sexta ( i x ) FEATURE:
        ( A ) NAME/KEY: CDS
        ( B ) LOCATION: 20..76

( x i ) SEQUENCE DESCRIPTION: SEQ ID NO:7:

GTCGATATCA TCAATCAAG ATG TAC AAG CTC ACA GTC TTC CTG ATG TTC ATC          52
                    Met Tyr Lys Leu Thr Val Phe Leu Met Phe Ile
                     1               5                  10

GCT TTC GTC ATC ATC GCT GAG GCC                                          76
Ala Phe Val Ile Ile Ala Glu Ala
             15

( 2 ) INFORMATION FOR SEQ ID NO:8:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

Met Tyr Lys Leu Thr Val Phe Leu Met Phe Ile Ala Phe Val Ile Ile
 1               5                  10                  15
Ala Glu Ala ( 2 ) INFORMATION FOR SEQ ID NO:9:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Manduca sexta (i x) FEATURE:
    (A) NAME/KEY: CDS
    (B) LOCATION: 13..81

(x i) SEQUENCE DESCRIPTION: SEQ ID NO:9:

```
CCCCCCGGAT CC ATG GCC GCT AAA TTC GTC GTG GTT CTG GCC GCT TGC        48
              Met Ala Ala Lys Phe Val Val Val Leu Ala Ala Cys
               1               5                      10

GTC GCC CTG AGC CAC TCG GCT ATG GTG CGC CGC                          81
Val Ala Leu Ser His Ser Ala Met Val Arg Arg
         15                  20
```

(2) INFORMATION FOR SEQ ID NO:10:

(i) SEQUENCE CHARACTERISTICS:
        (A) LENGTH: 23 amino acids
        (B) TYPE: amino acid
        (D) TOPOLOGY: linear (i i) MOLECULE TYPE: protein (x i) SEQUENCE DESCRIPTION: SEQ ID NO:10:

```
Met Ala Ala Lys Phe Val Val Val Leu Ala Ala Cys Val Ala Leu Ser
 1               5                  10                  15

His Ser Ala Met Val Arg Arg
             20
```

(2) INFORMATION FOR SEQ ID NO:11:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Manduca sexta (i x) FEATURE:
        (A) NAME/KEY: CDS
        (B) LOCATION: 21..89

(x i) SEQUENCE DESCRIPTION: SEQ ID NO:11:

```
TCCAGTCCAG TCACTTCATC ATG GCA GCC AAG TTC GTC GTG GTT CTC GCC        50
                      Met Ala Ala Lys Phe Val Val Val Leu Ala
                       1               5                  10

GCG TGC GTG GCC CTC TCG CAC AGC GCG ATG GTG CGC CGC                  89
Ala Cys Val Ala Leu Ser His Ser Ala Met Val Arg Arg
         15                  20
```

(2) INFORMATION FOR SEQ ID NO:12:

(i) SEQUENCE CHARACTERISTICS:
        (A) LENGTH: 23 amino acids
        (B) TYPE: amino acid
        (D) TOPOLOGY: linear (i i) MOLECULE TYPE: protein (x i) SEQUENCE DESCRIPTION: SEQ ID NO:12:

```
Met Ala Ala Lys Phe Val Val Val Leu Ala Ala Cys Val Ala Leu Ser
 1               5                  10                  15
```

His Ser Ala Met Val Arg Arg
                20

( 2 ) INFORMATION FOR SEQ ID NO:13:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bombyx mori ( i x ) FEATURE:
        ( A ) NAME/KEY: CDS
        ( B ) LOCATION: 13..75

( x i ) SEQUENCE DESCRIPTION: SEQ ID NO:13:

```
CCCCCCGGAT CC ATG TTC ACC TTC GCT ATT CTG CTC CTG TGC GTG CAA        48
              Met Phe Thr Phe Ala Ile Leu Leu Leu Cys Val Gln
               1               5                  10

GGC TGC CTG ATC CAG AAT GTT TAC GGA                                  75
Gly Cys Leu Ile Gln Asn Val Tyr Gly
         15                  20
```

( 2 ) INFORMATION FOR SEQ ID NO:14:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Phe Thr Phe Ala Ile Leu Leu Leu Cys Val Gln Gly Cys Leu Ile
 1               5                  10                  15

Gln Asn Val Tyr Gly
             20
```

( 2 ) INFORMATION FOR SEQ ID NO:15:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bombyx mori ( i x ) FEATURE:
        ( A ) NAME/KEY: CDS
        ( B ) LOCATION: 14..76

( x i ) SEQUENCE DESCRIPTION: SEQ ID NO:15:

```
AATATCCAGC ATC ATG TTT ACC TTC GCT ATT CTC CTT CTC TGC GTT CAG       49
               Met Phe Thr Phe Ala Ile Leu Leu Leu Cys Val Gln
                1               5                  10
```

```
GGT TGC CTG ATC CAA AAT GTG TAC GGT                                              76
Gly Cys Leu Ile Gln Asn Val Tyr Gly
            15                  20
```

( 2 ) INFORMATION FOR SEQ ID NO:16:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met Phe Thr Phe Ala Ile Leu Leu Leu Cys Val Gln Gly Cys Leu Ile
 1               5                  10                  15
Gln Asn Val Tyr Gly
            20
```

( 2 ) INFORMATION FOR SEQ ID NO:17:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Drosophila melanogaster ( i x ) FEATURE:
        ( A ) NAME/KEY: CDS
        ( B ) LOCATION: 13..60

( x i ) SEQUENCE DESCRIPTION: SEQ ID NO:17:

```
CCCCCCGGAT CC ATG TTC AAG TTC GTG ATG ATC TGC GCC GTC CTC GGC    48
          Met Phe Lys Phe Val Met Ile Cys Ala Val Leu Gly
           1               5                  10
CTG GCT GTG GCC                                                  60
Leu Ala Val Ala
        15
```

( 2 ) INFORMATION FOR SEQ ID NO:18:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met Phe Lys Phe Val Met Ile Cys Ala Val Leu Gly Leu Ala Val Ala
 1               5                  10                  15
```

( 2 ) INFORMATION FOR SEQ ID NO:19:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Drosophila melanogaster ( i x ) FEATURE:
    ( A ) NAME/KEY: CDS
    ( B ) LOCATION: 1..48

( x i ) SEQUENCE DESCRIPTION: SEQ ID NO:19:

```
ATG  TTC  AAG  TTT  GTC  ATG  ATC  TGC  GCA  GTT  TTG  GGC  CTG  GCG  GTG  GCC      48
Met  Phe  Lys  Phe  Val  Met  Ile  Cys  Ala  Val  Leu  Gly  Leu  Ala  Val  Ala
 1              5                        10                       15
```

( 2 ) INFORMATION FOR SEQ ID NO:20:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met  Phe  Lys  Phe  Val  Met  Ile  Cys  Ala  Val  Leu  Gly  Leu  Ala  Val  Ala
 1              5                        10                       15
```

( 2 ) INFORMATION FOR SEQ ID NO:21:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Drosophila melanogaster ( i x ) FEATURE:
        ( A ) NAME/KEY: CDS
        ( B ) LOCATION: 13..75

( x i ) SEQUENCE DESCRIPTION: SEQ ID NO:21:

```
CCCCCCGGAT CC  ATG  AAC  TAC  GTC  GGG  CTG  GGC  CTC  ATC  ATT  GTG  CTG      48
               Met  Asn  Tyr  Val  Gly  Leu  Gly  Leu  Ile  Ile  Val  Leu
                1                   5                        10

TCG  TGC  TTG  TGG  CTG  GGG  AGC  AAT  GCT                                    75
Ser  Cys  Leu  Trp  Leu  Gly  Ser  Asn  Ala
          15                        20
```

( 2 ) INFORMATION FOR SEQ ID NO:22:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met  Asn  Tyr  Val  Gly  Leu  Gly  Leu  Ile  Ile  Val  Leu  Ser  Cys  Leu  Trp
 1              5                        10                       15
```

Leu Gly Ser Asn Ala
             20

( 2 ) INFORMATION FOR SEQ ID NO:23:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Drosophila melanogaster ( i x ) FEATURE:
        ( A ) NAME/KEY: CDS
        ( B ) LOCATION: 25..87

( x i ) SEQUENCE DESCRIPTION: SEQ ID NO:23:

```
GAATTCGCCG GAGTGAGGAG CAAC ATG AAC TAC GTG GGA CTG GGA CTT ATC        51
                           Met Asn Tyr Val Gly Leu Gly Leu Ile
                            1               5

ATT GTG CTG AGC TGC CTT TGG CTC GGT TCG AAC GCG                       87
Ile Val Leu Ser Cys Leu Trp Leu Gly Ser Asn Ala
 10              15                  20
```

( 2 ) INFORMATION FOR SEQ ID NO:24:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Met Asn Tyr Val Gly Leu Gly Leu Ile Ile Val Leu Ser Cys Leu Trp
 1               5                  10                  15

Leu Gly Ser Asn Ala
             20
```

( 2 ) INFORMATION FOR SEQ ID NO:25:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bombyx mori ( i x ) FEATURE:
        ( A ) NAME/KEY: CDS
        ( B ) LOCATION: 13..57

( x i ) SEQUENCE DESCRIPTION: SEQ ID NO:25:

```
CCCCCCGGAT CC ATG CGC GTC CTG GTG CTG TTG GCC TGC CTG GCA GCC        48
              Met Arg Val Leu Val Leu Leu Ala Cys Leu Ala Ala
               1               5                   10
```

```
GCT AGC GCT                                                                                          57
Ala Ser Ala
        15
```

( 2 ) INFORMATION FOR SEQ ID NO:26:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: protein ( x i ) SEQUENCE DESCRIPTION: SEQ ID NO:26:

```
Met Arg Val Leu Val Leu Leu Ala Cys Leu Ala Ala Ala Ser Ala
 1           5                   10                  15
```

( 2 ) INFORMATION FOR SEQ ID NO:27:

( i ) SEQUENCE CHARACTERISTICS:
            ( A ) LENGTH: 65 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Bombyx mori ( i x ) FEATURE:
            ( A ) NAME/KEY: CDS
            ( B ) LOCATION: 21..65

( x i ) SEQUENCE DESCRIPTION: SEQ ID NO:27:

```
CACTCAGGAG TTCTTCAAAC ATG AGG GTT CTA GTA CTA CTG GCC TGC TTG            50
                     Met Arg Val Leu Val Leu Leu Ala Cys Leu
                      1           5                       10
GCC GCG GCG TCA GCC                                                      65
Ala Ala Ala Ser Ala
            15
```

( 2 ) INFORMATION FOR SEQ ID NO:28:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: protein ( x i ) SEQUENCE DESCRIPTION: SEQ ID NO:28:

```
Met Arg Val Leu Val Leu Leu Ala Cys Leu Ala Ala Ala Ser Ala
 1           5                   10                  15
```

( 2 ) INFORMATION FOR SEQ ID NO:29:

( i ) SEQUENCE CHARACTERISTICS:
            ( A ) LENGTH: 213 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO (i v) ANTI-SENSE: NO (v i) ORIGINAL SOURCE:
  (A) ORGANISM: Scorpion Androctonus Australis Hector (i x) FEATURE:
  (A) NAME/KEY: CDS
  (B) LOCATION: 1..213

(x i) SEQUENCE DESCRIPTION: SEQ ID NO:29:

| AAG | AAG | AAT | GGA | TAT | GCC | GTC | GAT | AGT | AGT | GGT | AAA | GCT | CCT | GAA | TGT | 48 |
|---|---|---|---|---|---|---|---|---|---|---|---|---|---|---|---|---|
| Lys | Lys | Asn | Gly | Tyr | Ala | Val | Asp | Ser | Ser | Gly | Lys | Ala | Pro | Glu | Cys | |
| 1 | | | | 5 | | | | | 10 | | | | | 15 | | |

| CTT | TTG | AGC | AAT | TAC | TGT | AAC | AAC | GAA | TGC | ACA | AAA | GTA | CAT | TAT | GCT | 96 |
|---|---|---|---|---|---|---|---|---|---|---|---|---|---|---|---|---|
| Leu | Leu | Ser | Asn | Tyr | Cys | Asn | Asn | Glu | Cys | Thr | Lys | Val | His | Tyr | Ala | |
| | | | 20 | | | | | 25 | | | | | 30 | | | |

| GAC | AAA | GGA | TAT | TGC | TGC | TTA | CTT | TCA | TGT | TAT | TGC | TTC | GGT | CTA | AAT | 144 |
|---|---|---|---|---|---|---|---|---|---|---|---|---|---|---|---|---|
| Asp | Lys | Gly | Tyr | Cys | Cys | Leu | Leu | Ser | Cys | Tyr | Cys | Phe | Gly | Leu | Asn | |
| | | 35 | | | | | 40 | | | | | 45 | | | | |

| GAC | GAT | AAA | AAA | GTT | TTG | GAG | ATT | TCG | GAC | ACA | AGG | AAA | AGT | TAT | TGT | 192 |
|---|---|---|---|---|---|---|---|---|---|---|---|---|---|---|---|---|
| Asp | Asp | Lys | Lys | Val | Leu | Glu | Ile | Ser | Asp | Thr | Arg | Lys | Ser | Tyr | Cys | |
| | 50 | | | | | 55 | | | | | 60 | | | | | |

| GAC | ACC | ACA | ATA | ATT | ATT | TAA | | | | | | | | | | 213 |
|---|---|---|---|---|---|---|---|---|---|---|---|---|---|---|---|---|
| Asp | Thr | Thr | Ile | Ile | Ile | | | | | | | | | | | |
| 65 | | | | | 70 | | | | | | | | | | | |

(2) INFORMATION FOR SEQ ID NO:30:

(i) SEQUENCE CHARACTERISTICS:
    (A) LENGTH: 70 amino acids
    (B) TYPE: amino acid
    (D) TOPOLOGY: linear (i i) MOLECULE TYPE: protein (x i) SEQUENCE DESCRIPTION: SEQ ID NO:30:

| Lys | Lys | Asn | Gly | Tyr | Ala | Val | Asp | Ser | Ser | Gly | Lys | Ala | Pro | Glu | Cys |
|---|---|---|---|---|---|---|---|---|---|---|---|---|---|---|---|
| 1 | | | | 5 | | | | | 10 | | | | | 15 | |

| Leu | Leu | Ser | Asn | Tyr | Cys | Asn | Asn | Glu | Cys | Thr | Lys | Val | His | Tyr | Ala |
|---|---|---|---|---|---|---|---|---|---|---|---|---|---|---|---|
| | | | 20 | | | | | 25 | | | | | 30 | | |

| Asp | Lys | Gly | Tyr | Cys | Cys | Leu | Leu | Ser | Cys | Tyr | Cys | Phe | Gly | Leu | Asn |
|---|---|---|---|---|---|---|---|---|---|---|---|---|---|---|---|
| | | 35 | | | | | 40 | | | | | 45 | | | |

| Asp | Asp | Lys | Lys | Val | Leu | Glu | Ile | Ser | Asp | Thr | Arg | Lys | Ser | Tyr | Cys |
|---|---|---|---|---|---|---|---|---|---|---|---|---|---|---|---|
| | 50 | | | | | 55 | | | | | 60 | | | | |

| Asp | Thr | Thr | Ile | Ile | Ile |
|---|---|---|---|---|---|
| 65 | | | | | 70 |

(2) INFORMATION FOR SEQ ID NO:31:

(i) SEQUENCE CHARACTERISTICS:
    (A) LENGTH: 213 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Scorpion Androctonus Australis Hector (i x) FEATURE:
    (A) NAME/KEY: CDS
    (B) LOCATION: 1..213

( x i ) SEQUENCE DESCRIPTION: SEQ ID NO:31:

| AAG | AAG | AAC | GGC | TAC | GCA | GTC | GAC | TCA | TCC | GGA | AAA | GCC | CCC | GAG | TGC | 48 |
| Lys | Lys | Asn | Gly | Tyr | Ala | Val | Asp | Ser | Ser | Gly | Lys | Ala | Pro | Glu | Cys | |
| 1 | | | | 5 | | | | | 10 | | | | | 15 | | |

| CTG | CTC | TCG | AAC | TAT | TGC | AAC | AAT | GAA | TGC | ACC | AAG | GTG | CAC | TAC | GCT | 96 |
| Leu | Leu | Ser | Asn | Tyr | Cys | Asn | Asn | Glu | Cys | Thr | Lys | Val | His | Tyr | Ala | |
| | | | 20 | | | | | 25 | | | | | 30 | | | |

| GAC | AAG | GGC | TAC | TGT | TGC | CTT | CTG | TCC | TGC | TAT | TGC | TTC | GGT | CTC | AAC | 144 |
| Asp | Lys | Gly | Tyr | Cys | Cys | Leu | Leu | Ser | Cys | Tyr | Cys | Phe | Gly | Leu | Asn | |
| | | 35 | | | | | 40 | | | | | 45 | | | | |

| GAC | GAC | AAG | AAA | GTT | CTG | GAA | ATC | TCT | GAT | ACT | CGC | AAG | AGC | TAC | TGT | 192 |
| Asp | Asp | Lys | Lys | Val | Leu | Glu | Ile | Ser | Asp | Thr | Arg | Lys | Ser | Tyr | Cys | |
| 50 | | | | | 55 | | | | | 60 | | | | | | |

| GAC | ACC | ACC | ATC | ATT | AAC | TAA | | | | | | | | | | 213 |
| Asp | Thr | Thr | Ile | Ile | Asn | | | | | | | | | | | |
| 65 | | | | | 70 | | | | | | | | | | | |

( 2 ) INFORMATION FOR SEQ ID NO:32:

( i ) SEQUENCE CHARACTERISTICS:
        ( A ) LENGTH: 70 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

| Lys | Lys | Asn | Gly | Tyr | Ala | Val | Asp | Ser | Ser | Gly | Lys | Ala | Pro | Glu | Cys |
| 1 | | | | 5 | | | | | 10 | | | | | 15 | |

| Leu | Leu | Ser | Asn | Tyr | Cys | Asn | Asn | Glu | Cys | Thr | Lys | Val | His | Tyr | Ala |
| | | | 20 | | | | | 25 | | | | | 30 | | |

| Asp | Lys | Gly | Tyr | Cys | Cys | Leu | Leu | Ser | Cys | Tyr | Cys | Phe | Gly | Leu | Asn |
| | | 35 | | | | | 40 | | | | | 45 | | | |

| Asp | Asp | Lys | Lys | Val | Leu | Glu | Ile | Ser | Asp | Thr | Arg | Lys | Ser | Tyr | Cys |
| | 50 | | | | | 55 | | | | | 60 | | | | |

| Asp | Thr | Thr | Ile | Ile | Asn |
| 65 | | | | | 70 |

( 2 ) INFORMATION FOR SEQ ID NO:33:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Scorpion Androctonus Australis Hector ( x i ) SEQUENCE DESCRIPTION: SEQ ID NO:33:

```
AGCCCCGAG TGCCTGCTCT CGAACTATTG CAACAATGAA TGCACCAAGG TGCACTACGC      60
TGACAAGGGC TACTGTTGCC TTCTGTCCTG CTATTGCTTC                          100
```

( 2 ) INFORMATION FOR SEQ ID NO:34:

( i ) SEQUENCE CHARACTERISTICS:
        ( A ) LENGTH: 110 base pairs
        ( B ) TYPE: nucleic acid
        ( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Scorpion Androctonus Australis Hector ( x i ) SEQUENCE DESCRIPTION: SEQ ID NO:34:

| | | | | | | |
|---|---|---|---|---|---|---|
| CTGTAGGTAC | CGGATCCTTA | GTTAATGATG | GTGGTGTCAC | AGTAGCTCTT | GCGAGTATCA | 60 |
| GAGATTTCCA | GAACTTTCTT | GTCGTCGTTG | AGACCGAAGC | AATAGCAGGA | | 110 |

( 2 ) INFORMATION FOR SEQ ID NO:35:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Scorpion Androctonus Australis Hector ( x i ) SEQUENCE DESCRIPTION: SEQ ID NO:35:

| | | | | | | |
|---|---|---|---|---|---|---|
| AGGCACTCGG | GGGCTTTTCC | GGATGAGGTC | GACTGCGTAG | CCGTTCTTCT | T | 51 |

( 2 ) INFORMATION FOR SEQ ID NO:36:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Human ( x i ) SEQUENCE DESCRIPTION: SEQ ID NO:36:

| | | | | | | |
|---|---|---|---|---|---|---|
| CCCCCCGGAT | CCATGTACCG | CATGCAGCTG | CTCTCCTGCA | TCGCCCTGTC | GCTGGCTCTG | 60 |
| GTGACCAATA | GCAAGAAGAA | CGGCTAC | | | | 87 |

( 2 ) INFORMATION FOR SEQ ID NO:37:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Manduca Sexta ( x i ) SEQUENCE DESCRIPTION: SEQ ID NO:37:

CCCCCCGGAT CCATGTACAA ACTGACCGTC TTCCTGATGT TCATCGCCTT CGTGATTATC        60

GCTGAGGCCA AGAAGAACGG CTAC        84

( 2 ) INFORMATION FOR SEQ ID NO:38:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bombyx mori ( x i ) SEQUENCE DESCRIPTION: SEQ ID NO:38:

CCCCCCGGAT CCATGTTCAC CTTCGCTATT CTGCTCCTGT GCGTGCAAGG CTGCCTGATC        60

CAGAATGTTT ACGGAAAGAA GAACGGCTAC        90

( 2 ) INFORMATION FOR SEQ ID NO:39:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Drosophila melanogaster ( x i ) SEQUENCE DESCRIPTION: SEQ ID NO:39:

CCCCCCGGAT CCATGAACTA CGTCGGGCTG GGCCTCATCA TTGTGCTGTC GTGCTTGTGG        60

CTGGGGAGCA ATGCTAAGAA GAACGGCTAC        90

( 2 ) INFORMATION FOR SEQ ID NO:40:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Manduca sexta ( x i ) SEQUENCE DESCRIPTION: SEQ ID NO:40:

CCCCCCGGAT CCATGGCCGC TAAATTCGTC GTGGTTCTGG CCGCTTGCGT CGCCCTGAGC        60

CACTCGGCTA TGGTGCGCCG CAAGAAGAAC GGCTAC        96

( 2 ) INFORMATION FOR SEQ ID NO:41:

( i ) SEQUENCE CHARACTERISTICS:
           ( A ) LENGTH: 72 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
           ( A ) ORGANISM: Bombyx mori ( x i ) SEQUENCE DESCRIPTION: SEQ ID NO:41:

```
CCCCCCGGAT  CCATGCGCGT  CCTGGTGCTG  TTGGCCTGCC  TGGCAGCCGC  TAGCGCTAAG        60

AAGAACGGCT  AC                                                                72
```

( 2 ) INFORMATION FOR SEQ ID NO:42:

( i ) SEQUENCE CHARACTERISTICS:
           ( A ) LENGTH: 75 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
           ( A ) ORGANISM: Drosophila melanogaster ( x i ) SEQUENCE DESCRIPTION: SEQ ID NO:42:

```
CCCCCCGGAT  CCATGTTCAA  GTTCGTGATG  ATCTGCGCCG  TCCTCGGCCT  GGCTGTGGCC        60

AAGAAGAACG  GCTAC                                                             75
```

( 2 ) INFORMATION FOR SEQ ID NO:43:

( i ) SEQUENCE CHARACTERISTICS:
           ( A ) LENGTH: 75 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
           ( A ) ORGANISM: Bombyx mori ( x i ) SEQUENCE DESCRIPTION: SEQ ID NO:43:

```
CCCCCCGGAT  CCATGAAACT  CCTGGTCGTG  TTCGCCATGT  GCGTGCCCGC  TGCCAGCGCT        60

AAGAAGAACG  GCTAC                                                             75
```

( 2 ) INFORMATION FOR SEQ ID NO:44:

( i ) SEQUENCE CHARACTERISTICS:
           ( A ) LENGTH: 60 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Scorpion Androctonus Australis Hector ( x i ) SEQUENCE DESCRIPTION: SEQ ID NO:44:

GATCCGATGA AATTTCTCCT ATTGTTTCTC GTAGTCCTTC AATAATGGG GGTGCTTGGC     60

( 2 ) INFORMATION FOR SEQ ID NO:45:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Scorpion Androctonus Australis Hector ( x i ) SEQUENCE DESCRIPTION: SEQ ID NO:45:

GCCAAGCACC CCCATTATTG GAAGGACTAC GAGAAACAAT AGGAGAAATT TCATCG     56

( 2 ) INFORMATION FOR SEQ ID NO:46:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Scorpion Androctonus Australis Hector ( x i ) SEQUENCE DESCRIPTION: SEQ ID NO:46:

AAGAAGAATG GATATGCCGT CGATAGTAGT GGTAAAGCTC     40

( 2 ) INFORMATION FOR SEQ ID NO:47:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Scorpion Androctonus Australis Hector ( x i ) SEQUENCE DESCRIPTION: SEQ ID NO:47:

CTCAAAAGAC ATTCAGGAGC TTTACCACTA CTATCGACGG CATATCCATT CTTCTT     56

5,547,871

( 2 ) INFORMATION FOR SEQ ID NO:48:

( i ) SEQUENCE CHARACTERISTICS:
          ( A ) LENGTH: 56 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( A ) ORGANISM: Scorpion Androctonus Australis Hector ( x i ) SEQUENCE DESCRIPTION: SEQ ID NO:48:

CTGAATGTCT TTTGAGCAAT TACTGTAACA ACGAATGCAC AAAAGTACAT TATGCT     56

( 2 ) INFORMATION FOR SEQ ID NO:49:

( i ) SEQUENCE CHARACTERISTICS:
          ( A ) LENGTH: 57 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( A ) ORGANISM: Scorpion Androctonus Australis Hector ( x i ) SEQUENCE DESCRIPTION: SEQ ID NO:49:

CAGCAATATC CTTTGTCAGC ATAATGTACT TTTGTGCATT CGTTGTTACA GTAATTG     57

( 2 ) INFORMATION FOR SEQ ID NO:50:

( i ) SEQUENCE CHARACTERISTICS:
          ( A ) LENGTH: 66 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( A ) ORGANISM: Scorpion Androctonus Australis Hector ( x i ) SEQUENCE DESCRIPTION: SEQ ID NO:50:

GACAAAGGAT ATTGCTGCTT ACTTTCATGT TATTGCTTCG GTCTAAATGA CGATAAAAAA     60

GTTTTG     66

( 2 ) INFORMATION FOR SEQ ID NO:51:

( i ) SEQUENCE CHARACTERISTICS:
          ( A ) LENGTH: 66 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO

```
          ( i v ) ANTI-SENSE: NO ( v i ) ORIGINAL SOURCE:
                    ( A ) ORGANISM: Scorpion Androctonus Australis Hector ( x i ) SEQUENCE DESCRIPTION: SEQ ID NO:51:

CTTGTGTCCG  AAATCTCCAA  AACTTTTTA   TCGTCATTTA  GACCGAAGCA  ATAACATGAA        6 0

AGTAAG                                                                        6 6

( 2 ) INFORMATION FOR SEQ ID NO:52:

( i ) SEQUENCE CHARACTERISTICS:
                    ( A ) LENGTH: 52 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: Scorpion Androctonus Australis Hector ( x i ) SEQUENCE DESCRIPTION: SEQ ID NO:52:

GAGATTTCGG  ACACAAGGAA  AAGTTATTGT  GACACCACAA  TAATTAATTA  AG                5 2

( 2 ) INFORMATION FOR SEQ ID NO:53:

( i ) SEQUENCE CHARACTERISTICS:
                    ( A ) LENGTH: 39 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: Scorpion Androctonus Australis Hector ( x i ) SEQUENCE DESCRIPTION: SEQ ID NO:53:

AATTCTTAAT  TAATTATTGT  GGTGTCACAA  TAACTTTTC                                 3 9
```

HETEROLOGOUS SIGNAL SEQUENCES FOR SECRETION OF INSECT CONTROLLING PROTEINS

FIELD OF THE INVENTION

This invention relates to the identification of heterologous signal sequences which facilitate the expression and secretion of insect contolling proteins, and the demonstration of in vivo toxicity of insect viruses encoding those proteins.

BACKGROUND OF THE INVENTION

The following abbreviations are used throughout this application:
A. cal.—*Autographa californica*
AcMNPV—*Autographa californica* nuclear polyhedrosis virus
AaIT—*Androctonus australis* insect toxin
bp—base pairs
CPU—contractile paralysis unit
ECV—extracellular virus
GV—granulosis virus
kD—kilodaltons
LT—lethality time
MOI—multiplicity of infection
NPV—nuclear polyhedrosis virus
OB—occlusion body
Occ—occlusion negative virus(es)
Occ+—occlusion positive virus(es)
PCR—polymerase chain reaction
PDV—polyhedron derived virus
PFU—plaque forming unit
p.i.—post-infection
PIB—polyhedron inclusion body (also known as OB)
ST—survival time The family of DNA insect viruses known as Baculoviridae includes nuclear polyhedrosis viruses (NPV) and granulosis viruses (GV). These viruses produce occlusion bodies (OBs) in their life cycle. Also included are the non-occluded viruses (NOV), which do not produce OBs in their life cycle. Another family of DNA insect viruses are the entomopox viruses.

Over 400 baculoviruses have been identified as present in invertebrates. Examples of NPVs include *Lymantria dispar* NPV (gypsy moth NPV), *Autographa californica* MNPV, *Syngrapha falcifera* NPV (celery looper NPV), *Spodoptera litturalis* NPV, *Spodoptera frugiperda* NPV, *Heliothis armigera* NPV, *Mamestra brassicae* NPV, *Choristoneura fumiferana* NPV, *Trichoplusia ni* NPV, *Helicoverpa zea* NPV, etc. Examples of GVs include *Cydia pomonella* GV (codling moth GV), *Pieris brassicae* GV, *Trichoplusia ni* GV, etc. Examples of NOVs are *Orcytes rhinoceros* NOV and *Hleiothis zea* NOV. Examples of entomopox viruses include *Melolontha melonotha* EPV, *Amsacta moorei* EPV, *Locusta migratoria* EPV, *Melanoplus sanguinipes* EPV, *Schistocerca gregaria* EPV, *Aedes aegypti* EPV, *Chironomus luridus* EPV, etc.

The use of baculoviruses and entomopox viruses as bioinsecticides holds great promise. One of the major impediments to their widespread use in agriculture is the time lag between initial infection of the insect and its death. This lag can range from a few days to several weeks. During this lag, the insect continues to feed, causing further damage to the plant. A number of researchers have attempted to overcome this drawback by inserting a heterologous gene into the viral genome, so as to express an insect controlling or modifying substance, such as a toxin, neuropeptide or an enzyme (Bibliography entries 1–5).

The life cycle of baculoviruses, as exemplified by AcMNPV, includes two stages. Each stage of the life cycle is represented by a specific form of the virus: Extracellular viral particles (ECV) which are nonoccluded, and occluded virus particles (OB) (6,7). The extracellular and occluded virus forms have the same genome, but exhibit different biological properties. The maturation of each of the two forms of the virus is directed by overlapping sets of vital genes, some of which are unique to each form.

In its naturally occurring insect infectious form, multiple virions are found embedded in a paracrystalline protein matrix known as an occlusion body (OB), which is also referred to as a polyhedron inclusion body (PIB). The proteinaceous vital occlusions are referred to as polyhedra (polyhedron is the singular term). A polyhedrin protein, which has a molecular weight of 29 kD, is the major viral-encoded structural protein of the vital occlusions (6,8). (Similarly, GVs produce OBs which are composed primarily of granulin, rather than polyhedrin).

The viral occlusions are an important part of the natural baculovirus life cycle, providing the means for horizontal (insect to insect) transmission among susceptible insect species. In the environment, a susceptible insect (usually in the larval stage) ingests the viral occlusions from a contaminated food source, such as a plant. The crystalline occlusions dissociate in the gut of the susceptible insects to release the infectious vital particles. These polyhedron derived viruses (PDV) invade and replicate in the cells of the midgut tissue (6).

It is believed that virus particles enter the cell by endocytosis or fusion, and the viral DNA is uncoated at the nuclear pore or in the nucleus. Viral DNA replication is detected within six hours. By 10–12 hours post-infection (p.i.), secondary infection spreads to other insect tissues by the budding of the extracellular virus (ECV) from the surface of the cell. The ECV form of the virus is responsible for cell to cell spread of the virus within an individual infected insect, as well as transmitting infection in cell culture.

Late in the infection cycle (12 hours p.i.), polyhedrin protein can be detected in infected cells. It is not until 18–24 hours p.i. that the polyhedrin protein assembles in the nucleus of the infected cell and virus particles become embedded in the proteinaceous occlusions. Viral occlusions accumulate to large numbers over 4–5 days as cells lyse. These polyhedra have no active role in the spread of infection in the larva. ECVs in the haemolymph multiply and spread, leading to the death of the larva (6–8).

When infected larvae die, millions of polyhedra remain in the decomposing tissue, while the ECVs are degraded. When other larvae are exposed to the polyhedra, for example, by ingestion of contaminated plants or other food material, the cycle is repeated (6).

In summary, the occluded form of the virus is responsible for the initial infection of the insect through the gut, as well as the environmental stability of the virus. PDVs are essentially not infectious when administered by injection, but are highly infectious orally. The non-occluded form of the virus (i.e., ECV) is responsible for secondary and cell to cell infection. ECVs are highly infectious for cells in culture or internal insect tissues by injection, but essentially not infectious by oral administration.

The use of recombinant baculoviruses expressing foreign proteins which are toxic to insects is facilitated by the fact that these viruses are not pathogenic to vertebrates or plants. In addition, the baculoviruses generally have a narrow host range. Many strains are limited to one or a few insect species.

The *Autographa californica* nuclear polyhedrosis virus (AcMNPV) is the prototype virus of the family Baculoviridae. The AcMNPV virus was originally isolated from *Autographa californica* (*A. cal.*), a lepidopteran noctuid (which in its adult stage is a nocturnal moth), commonly known as the alfalfa looper. This virus infects 12 families and more than 30 species within the order of Lepidoptera insects (9). It is not known to infect productively any species outside this order. The most widely studied baculovirus is AcMNPV. This virus utilizes many of the protein maturation and transport systems that occur in higher eukaryotic cells.

In this invention, a gene coding for an insect controlling protein is inserted into a suitable location in the viral genome. Heterologous genes inserted into AcMNPV produce proteins which are biologically active in the infected insect cells. These proteins, for the most part, undergo post-translational processing to produce and secrete recombinant products very similar, if not identical, to those of authentic proteins. A protein thus expressed enhances the bioinsecticidal effect of the virus.

One such protein is the toxin designated AaIT, which is produced by the venom of the North African scorpion *Androctonus australis* Hector. The toxin is 70 amino acids in length and binds to sodium channels in insects and causes contractile paralysis at the nanogram to picogram range in insect larvae. Because AaIT does not bind to mammalian sodium channels, AaIT is a candidate for use as a bioinsecticide to protect crops ingested by humans.

The region upstream of the coding region of the AaIT gene includes a signal sequence which directs the secretion of AaIT from the cell. Specifically, the signal sequence directs the toxin through the secretory pathway to the cell surface where it is secreted from the cell. During transport, enzymes cleave the signal sequence, leaving the mature AaIT.

There is a continuing need for genetically engineered recombinant insect viruses which express heterologous toxins in infected hosts. Infection by these recombinant viruses increases the speed of kill when compared with the wild-type virus.

SUMMARY OF THE INVENTION

This invention provides for seven specific heterologous signal sequences for use with a DNA sequence encoding an insect controlling protein. In particular, this invention provides for the use of one of those heterologous signal sequences with the DNA sequence encoding the insect-specific toxin AaIT. The DNA sequence encoding AaIT may be the native sequence or a codon optimized sequence. A heterologous signal sequence and the codon optimized AaIT DNA sequence are then inserted into an insect virus such as the baculovirus AcMNPV.

The baculovirus infects specific susceptible insect target species, resulting in the eventual death of the insect in its larval stage. The toxin AaIT produced by a scorpion is also specific for susceptible insect target species (but not vertebrates) and causes paralysis and ultimately death of the insect.

The insertion of the gene encoding AaIT and a heterologous signal sequence into a baculovirus results in the expression and secretion of the toxin. A susceptible insect which ingests such a modified baculovirus will cease feeding on plants due to toxin-induced parlysis at an earlier time than an insect which ingests a wild-type baculovirus lacking an AaIT gene. The greater the reduction in time, the greater the reduction of damage to crops, because the period of larval feeding is reduced. Thus, this invention provides a method for protecting plants from damage from insects, by delivering to the plant (through spraying or other delivery means) an expression vector incorporating the AaIT gene, together with a heterologous signal sequence.

Eight heterologous signal sequences are initially constructed. In an injection bioassay, recombinant viruses containing any one of seven of these signal sequences, linked to an AaIT gene, demonstrate an earlier onset of morbidity than a wild-type insect virus which lacks the AaIT gene. The seven heterologous signal sequences used in this invention, which may be a codon optimized sequence or the native sequence, are the pBMHPC-12 signal sequence from *Bombyx mori* (SEQ ID NOS: 1 and 3), the adipokinetic hormone signal sequence from *Manduca sexta* (SEQ ID NOS: 5 and 7), the apolipophorin signal sequence from *Manduca sexta* (SEQ ID NOS: 9 and 11), the chorion signal sequence from *Bombyx mori* (SEQ ID NOS: 13 and 15), the cuticle signal sequence from *Drosophila melanogaster* (SEQ ID NOS: 17 and 19), the esterase-6 signal sequence from *Drosophila melanogaster* (SEQ ID NOS: 21 and 23) and the sex specific signal sequence from *Bombyx mori* (SEQ ID NOS: 25 and 27)(in each pair of sequence listings, the codon optimized sequence is the first number). As exemplified with AaIT, each signal sequence is located immediately upstream of either a codon optimized DNA sequence encoding AaIT (SEQ ID NO. 31) or the native DNA sequence encoding AaIT (SEQ ID NO: 29). Each such DNA sequence construct is then inserted into an expression vector.

When the expression vector containing such a heterologous signal sequence-AaIT construct is used to transform or infect into a suitable host cell, AaIT is expressed. The signal sequence assists in the secretion of AaIT and is then cleaved off by a signal peptidase, leaving the mature form of AaIT (70 amino acids)(SEQ ID NO: 31).

Each heterologous signal sequence of this invention may have the native nucleotide sequence encoding the signal sequence. Alternatively, each signal sequence may have a codon optimized nucleotide sequence encoding the same signal sequence.

The degeneracy of the genetic code permits variations of the nucleotide sequence, while still producing a polypeptide (such as a signal sequence) having the identical amino acid sequence as the polypeptide encoded by the native DNA sequence.

The frequency of individual synonymous codons for cognate amino acids varies widely from genome to genome among eucaryotes and procaryotes. These differences in codon choice patterns appear to contribute to the overall expression levels of individual genes by modulating peptide elongation rates.

In one embodiment of this invention, codon optimized signal sequences are designed using the same principles as the AaIT gene whose toxin the signal sequence is responsible for secreting. It is first attempted to have the preferred codon usage frequencies for this synthetic gene and signal sequence reflect the codon usages of genes derived from the genome of the cell/organism to be used for recombinant protein expression. However, adequate representation for both lepidopteran gene sequences and insect viral gene sequences was not available at the time of this invention to create a reliable codon usage table, because there was DNA sequence information available from only a small number of genes.

Therefore, codon use tables are taken from a species, *Drosophila melanogaster,* which has a sufficient number (at least 10) of known gene sequences. These codon use tables are used to design the codon optimized gene encoding AaIT and each heterologous signal sequence gene. This methodology also permits the preservation or destruction (if desired) of restriction enzyme recognition sites. The codon use frequency for each amino acid of AaIT reflects frequencies in *Drosophila melanogaster* codon use tables.

The codon optimized sequences for the heterologous signal sequences and the AaIT gene encode the identical amino acid sequences as the native nucleotide sequences encoding the native signal sequences and AaIT, respectively.

BRIEF DESCRIPTION OF THE DRAWINGS

FIG. 1 depicts a comparison of the nucleotide sequences of of native and codon optimized genes encoding AaIT, together with the amino acid sequence of AaIT.

FIG. 2 depicts detail of the construction of the plasmid pBS Cuticle-AaIT, which contains the heterologous cuticle signal sequence and a codon optimized cDNA sequence encoding AaIT.

FIG. 3 depicts detail of the construction of the plasmid pBS GIII-AaIT, which contains the native signal sequence and the native cDNA sequence encoding AaIT.

FIG. 4 depicts the levels of toxin-encoding RNA as a percentage of polyhedrin RNA which accumulates in Sf9 cells infected with wild-type AcMNPV. A DNA probe detects the 3' untranslated region common to both toxin and polyhedrin RNAs. The bars on the X axis are as follows: Mock (non-infected); Wild Type (wild-type AcMNPV); Es6-AaIT (AcMNPV containing esterase-6 signal sequence and codon optimized AaIT gene); ADK-AaIT (AcMNPV containing adipokinetic signal sequence and codon optimized AaIT gene); Cut-AaIT (AcMNPV containing cuticle signal sequence and codon optimized AaIT gene); pBM-AaIT (AcMNPV containing pBMHPC-12 signal sequence and codon optimized AaIT gene); Chor-AaIT (AcMNPV containing Chorion signal sequence and codon optimized AaIT gene); Apo-AaIT (AcMNPV containing apolipophorin signal sequence and codon optimized AaIT gene); Sex-AaIT (AcMNPV containing sex specific signal sequence and codon optimized AaIT gene); and grp III-AaIT (AcMNPV containing native signal sequence and native AaIT gene).

FIG. 5 depicts graphs of the response time of *H. virescens* larvae in a vital injection assay. In Panel A, larvae receive either no virus (negative control)(80 insects) or 100, 1000 or 10,000 PFU of wild-type AcMNPV (Strain E2)(48 insects each). In Panel B, larvae receive either no virus (negative control)(80 insects) or 100, 1000 or 10,000 PFU of AcMNPV which contains the cuticle signal sequence and a codon optimized cDNA encoding AaIT (48 insects each).

FIGS. 6–15 depict graphs of the toxicity of viruses, presented as a percentage of larvae responding at various time intervals to the indicated doses of virus present in a microdrop of ingested diet. FIG. 6 depicts wild-type AcMNPV (Strain E2), which is used as a control for FIGS. 7–10. FIG. 7 depicts an esterase-6-AaIT-virus construct. FIG. 8 depicts an adipokinetic hormone-AaIT-virus construct. FIG. 9 depicts a cuticle-AaIT-virus construct. FIG. 10 depicts the native signal-native AaIT-virus construct. FIG. 11 depicts wild-type AcMNPV (Strain E2), which is used as a control for FIGS. 12–15. FIG. 12 depicts a pBMHPC-12-AaIT-virus construct. FIG. 13 depicts a chorion-AaIT-virus construct. FIG. 14 depicts an apolipophorin-6-AaIT-virus construct. FIG. 15 depicts a sex-specific-AaIT-virus construct. The constructs in FIGS. 7–9 and 12–15 include a codon optimized AaIT gene.

DETAILED DESCRIPTION OF THE INVENTION

Heterologous signals which process (cleave and export) an insect controlling protein are the subject of this invention. Lethality of an insect virus is facilitated by the use of any one of seven specific heterologous signal sequences with the gene for the insect controlling protein.

Signal sequences are required for a complex series of post-translational processing steps which result in secretion of a protein. If an intact signal sequence is present, the protein being expressed enters the lumen of the-rough endoplasmic reticulum and is then transported through the Golgi apparatus to secretory vesicles and is finally transported out of the cell. Generally, the signal sequence immediately follows the initiation codon and encodes a signal peptide at the amino-terminal end of the protein to be secreted. In most cases, the signal sequence is cleaved off by a specific protease, called a signal peptidase. Preferred signal sequences improve the processing and export efficiency of recombinant protein expression using viral expression vectors. Optimized expression of the insect controlling protein using an appropriate heterologous signal sequence achieves more rapid lethality than wild-type insect virus.

Summers U.S. Pat. No. 5,155,037 (10) describes the use of insect signal sequences such as adipokinetic hormone and cuticle in a Lepidopteran insect cell transformed or transfected with a DNA vector, where said signal directs the secretion of a heterologous protein from the insect cell. The only foreign proteins disclosed are CD4, interleukin-2 and beta-interferon. All of these proteins are mammalian proteins; none is an insect controlling protein. Prior to U.S. Pat. No. 5,155,037, the only method of achieving secretion of a foreign protein in insect cells was by using the foreign gene's native signal peptide. Because the foreign genes are usually from non-insects, their signals may be poorly recognized by insect cells, resulting in suboptimal levels of expression. The signal sequence is generally coded by a DNA sequence immediately following (5' to 3') the translation start site of the foreign gene. Proteins secreted from cells are synthesized as precursor molecules containing hydrophobic N-terminal signal peptides.

A secretory signal sequence contains three regions: A basic N-terminal region (n-region); a central hydrophobic region (h-region); and a more polar C-terminal region (c-region) (11). Cleavage of the signal sequence from the mature protein once export is under way appears to be dependent upon structures in the n- and h- regions; however, positions −3 and −1 relative to the cleavage site (in the c- region) have been suggested to be the most important (11). The residue in position −1 should be small (alanine, serine, glycine, cysteine, threonine or glutamine), while the residue in position −3 should not be aromatic (phenylalanine, histidine, tyrosine or tryptophan), charged (asparagine, glutamic acid, lysine or arginine) or large and polar (asparagine or glutamine), with proline being absent from the region −3 to +1. Some exceptions to these parameters are permitted (11).

This −3, −1 rule is 75–80% predictive of the cleavage site in mammalian systems (11), but has not been confirmed in insect systems.

Summers U.S. Pat. No. 5,155,037 (10) describes the sequence encoding the Lepidopteran (*Manduca sexta*) adipokinetic hormone signal peptide. This is a short signal peptide (19 amino acids) for a blocked neuropeptide that regulates energy substrate mobilization and metabolism in insects. FIG. 2B of the patent depicts the nucleotide and amino acid sequences of the signal peptide.

The patent also describes the sequence encoding *Drosophila melanogaster* cuticle signal peptide. FIG. 2A of the patent depicts the nucleotide and amino acid sequences of the cuticle gene CP1 leader peptide. The nucleotide sequence codes for a 16 amino acid signal peptide.

Eight constructs with heterologous signal sequences are prepared by Applicants. The DNA sequences encoding these signal sequences can be either the native DNA sequences encoding the signal sequences or codon optimized DNA sequences encoding those signal sequences. One such signal sequence is the combined with a gene encoding an insect controlling protein. Each such construct is then inserted into a baculovirus transfer vector and then moved into the genome of an insect virus by homologous DNA recombination in cultured cells (12).

The heterologous signal sequences are as follows: Interleukin-2, Esterase-6, Adipokinetic hormone, Cuticle, pBMHPC-12, Chorion, Apolipophorin and Sex Specific.

Interleukin-2 is a human signal sequence (for a T-cell growth factor) whose use with AaIT has previously been described (13). The adipokinetic hormone signal sequence (for a neuropeptide) is from Manduca sexta and fits the −3, −1 rule (11) well. The chorion signal sequence from *Bombyx mori* (for an eggshell structural protein) and the cuticle signal sequence of *Drosophila melanogaster* (for an exoskeletal protein) both secrete a large quantity of their associated mature proteins. The apolipophorin signal sequence from *Manduca sexta* (for a plasma lipid transport protein), the sex specific signal sequence of *Bombyx mori* (for a major adult plasma storage protein) and the pBMHPC-12 signal sequence from *Bombyx mori* (for a 30 kD larval plasma lipoprotein) all are selected because they are found in fat body cells and and each secrete a hemolymph protein. Finally, the esterase-6 signal sequence is used for the secretion of a serine hydrolase from *Drosophila melanogaster.* Each of these signal sequences except apoliphophorin complies with the −3, −1 rule (11) for predicting the cleavage site.

The degeneracy of the genetic code permits variations of the nucleotide sequence, while still producing a polypeptide having the identical amino acid sequence as the polypeptide encoded by the native DNA sequence. The procedure known as codon optimization provides one with a means of designing such an altered DNA sequence.

The design of codon optimized genes should take into account a variety of factors, including the frequency of codon usage in an organism, nearest neighbor frequencies, RNA stability, the potential for secondary structure formation, the route of synthesis and the intended future DNA manipulations of that gene.

The degeneracy of the genetic code permits the same amino acid sequence to be encoded and translated in many different ways. For example, leucine, serine and arginine are each encoded by six different codons, while valine, proline, threonine, alanine and glycine are each encoded by four different codons.

However, the frequency of use of such synonymous codons varies from genome to genome among eucaryotes and procaryotes. For example, synonymous codon-choice patterns among mammals are very similar, while evolutionarily distant organisms such as yeast (*S. cerevisiae*), bacteria (such as *E. coli*) and insects (such as *D. melanogaster*) reveal a clearly different pattern of genomic codon use frequencies (14–19).

These differences in codon-choice patterns appear to contribute to the overall expression levels of individual genes by modulating peptide elongation rates. Two lines of experimental evidence support this argument. First, the rate of polypeptide synthesis depends on the character of the codons being translated, as well as the initial kinetics for transfer RNA ("tRNA") ternary complex formation (19–24). Second, cellular transfer RNA distributions tend to follow the cognate codon frequencies of the messenger RNA ("mRNA") pool (24–27).

For these reasons, it is desirable and useful to design genes intended for insect virus expression systems where the codon frequencies reflect the cognate cellular tRNA frequencies. This is particularly desirable for expression systems like the baculovirus expression system using the polyhedrin promoter, where a single mRNA specie may utilize over one-half the cellular translation capacity. Hence, codon frequency really should reflect the cognate cellular tRNA frequencies when expressing recombinant protein at high levels.

The preferred codon usage frequencies for a synthetic gene should reflect the codon usages of nuclear genes derived from the exact (or as closely related as possible) genome of the cell/organism that is intended to be used for recombinant protein expression.

In the present invention, adequate representation for both lepidopteran gene sequences and insect viral gene sequences was not available at the time of this invention to create a reliable codon usage table for these initial experiments. Ikemura et al. have cautioned that reliable codon-choice patterns require the summation of codon frequencies from ten or more genes with varying functions (16,28). This codon optimized sequence is intended to be expressed in a variety of insects, not just those infected by AcMNPV. Therefore, it is of primary importance that the codon optimization be compatible with tRNA pool distribution in a variety of insect cells.

For this reason, an insect specie is selected which has a sufficient number of known gene sequences. *Drosophila melanogaster* has codon use tables derived from 44 nuclear genes totalling 20,451 codons (17). These codon use tables are used to design the codon optimized genes encoding signal sequences of this invention and the AaIT toxin sequence described below.

A gene for a full length signal peptide sequence is fused to a gene for an insect controlling protein, such as a codon optimized AaIT toxin peptide sequence (described below). As discussed above, the signal sequences may be encoded by native or codon optimized nucleotide sequences encoding heterologous signal sequences.

These amino acid sequences are reverse-translated into a DNA sequence showing all possible nucleotide degeneracies (maximum ambiguity). A list of definite and potential (because of codon degeneracies) restriction enzyme recognition sites is generated. Restriction enzyme sites critical for gene synthesis as well as for the convenience of additional DNA manipulation are selected and preserved. One important advantage of assigning codons during the design of optimized genes is that restriction enzyme sites can be readily preserved or destroyed at the convenience of one skilled in the art to facilitate gene contruction and manipulation.

A list recording the number of times each amino acid occurs in the insect controlling protein and each signal sequence is generated. Codons are assigned on the basis of the number of amino acid residues present in the sequence to reflect the relative frequency of *Drosophila melanogaster* codon use (17).

For example, the cysteine codon frequency in *Drosophila melanogaster* is 76% for the sequence TGC and 24% for the sequence TGT. There are eight cysteine residues in the ADK signal-AaIT gene construct (all in the gene coding for the mature AaIT protein (SEQ ID NO: 31)). Hence, six codons are allocated as TGC (75% of the residues) and two codons as TGT (25% of the residues). Based on this distribution, each cysteine codon is then assigned an exact, unambiguous sequence. Attention is given to alternating adjacent isocodons. For example, the two adjacent cysteine residues in the AaIT peptide (amino acids 37 and 38) are assigned the sequence TGC TGC to avoid assigning two identical codon sequences sequentially.

This process is repeated for all twenty amino acids and the termination codon (although the termination codon sequence TAA is not changed by this procedure). In addition, all critical restriction enzyme sites are preserved and unwanted sites are destroyed.

The codon optimized nucleic acid sequences are synthesized and assembled using conventional techniques. Example 2 below describes one such method using a series of synthetic oligonucleotide fragments which are then joined to form the complete signal and protein coding sequences.

The codon optimized signal sequences differ from the native sequences as follows: pBMHPC-12—7 of 48 nucleotides (compare SEQ ID NO: 1 (codon optimized) and SEQ ID NO: 3 (native)); adipokinetic hormone—6 of 57 nucleotides (compare SEQ ID NO: 5 (codon optimized) and SEQ ID NO: 7 (native)); apolipophorin—14 of 69 nucleotides (compare SEQ ID NO: 9 (codon optimized) and SEQ ID NO: 11 (native)); chorion—10 of 63 nucleotides (compare SEQ ID NO: 13 (codon optimized) and SEQ ID NO: 15 (native)); cuticle—6 of 48 nucleotides (compare SEQ ID NO: 17 (codon optimized) and SEQ ID NO: 19 (native)); esterase-6—15 of 63 nucleotides (compare SEQ ID NO: 21 (codon optimized) and SEQ ID NO: 23 (native)); sex-specific—15 of 45 nucleotides (compare SEQ ID NO: 25 (codon optimized) and SEQ ID NO: 27 (native)). However, the amino acids of the signal sequences encoded by the differing nucleic acid sequences are identical for both the codon optimized and native sequences.

The heterologous signal sequences of the present invention are used with an insect controlling protein. These proteins are toxins, neuropeptides and enzymes. In addition to AaIT described above, examples of such toxins include a toxin from the mite species *Pyemotes tritici* (29), the *Bacillus thuringiensis* subsp. aizawai toxin (30) and the *Bacillus thuringiensis* CryIVD toxin (31). Examples of neuropeptides include eclosion hormone (4), prothoracicotropic hormone, adipokinetic hormone, diuretic hormone and proctolin (32). Examples of enzymes include juvenile hormone esterase and derivatives thereof (5).

The isolated nucleic acid sequence encoding the heterologous signal sequence and the insect controlling protein is then inserted into an expression vector which is appropriate for the host cell or organism in which the protein is to be produced. The DNA sequence can be inserted directly into the expression vector or can be inserted with the aid of a transfer vector.

For example, these heterologous signal sequences may be used with native or codon optimized DNA sequences encoding the insect-specific toxin AaIT. The insertion of the gene encoding AaIT into an insect virus results in the expression of the toxin, which is responsible for a reduction in the time needed for the virus to incapacitate and kill larvae. A susceptible insect which ingests such a modified insect virus will cease feeding on plants at an earlier time than an insect which ingests a wild-type insect virus lacking an AaIT gene. The greater the reduction in time, the greater the reduction of damage to crops, because the period of larval feeding is reduced.

The complete codon optimized sequence of the AaIT gene (SEQ ID NO: 21) used with the heterologous signal sequences is constructed according to the principles described above. This sequence differs from the native cDNA sequence encoding AaIT (SEQ ID NO: 29) by 58 out of 210 nucleotides (see FIG. 1). However, the AaIT produced by the native cDNA and the codon optimized cDNA have identical amino acid sequences. If desired, the signal sequence for AaIT may also be codon optimized by the same procedures just described.

Once the synthetic gene containing the codon optimized nucleic acid sequence is constructed (or the native gene is isolated), the gene is inserted into an appropriate expression vector, by conventional techniques such as cloning into the vector after digestion with one or more appropriate restriction enzymes. Smith and Summers U.S. Pat. No. 4,745,051 (8) describes the construction of baculovirus expression vectors, which are recombinant insect viruses in which the coding sequence for a foreign gene is inserted behind a baculovirus promoter in place of the viral polyhedrin gene. The polyhedrin gene is nonessential for productive vital infection between cells.

Transfer vectors are used as tools to transfer foreign genes into a viral genome. Transfer vectors generally are bacterial plasmids containing sufficient viral sequences to facilitate insertion of the foreign gene into the viral genome by homologous recombination.

Methods for constructing recombinant baculoviruses in insect cells are set forth in M. D. Summers and G. E. Smith, *A Manual of Methods for Baculovirus Vectors and Insect Cell Culture Procedures*, Texas Agricultural Experimental Station Bull. No. 1555 (1987) (12)). A preferred cell line is that of Sf9 cells (ATCC accession number CRL1711), which are derivatives of the cell line designated *Spodoptera frugiperda* 21 (Sf21). Other insect cell lines that are adequate for propagation of a desirable insect virus include those derived from *Trichoplusia ni* (TN368), the silkworm *Bombyx mori* (BM) and *Helicoverpa zea* (BCIRL-Hz-Aml, BCIRL-Hz-Am3).

Suitable insect viruses include those listed above in the Background of the Invention. A preferred insect virus is the baculovirus AcMNPV. A particular strain of AcMNPV designated E2 is used in the Examples. Those of skill in the art will recognize that other baculovirus strains may also be used. These include *Trichoplusia ni* MNPV, *Rachiplusia ou* MNPV, *Galleria mallonella* MNPV, *Spodoptera frugiperda* NPV and plaque-purified strains such as the M3, R9, S1 and S3 strains of AcMNPV isolated and characterized in Smith, G. E., and Summers, M. D., *J. Virol.*, 33, 311–319 (1980) (33), as well as *Bombyx mori* NPV. See also Smith, G. E., and Summers, M. D., *Virol.*, 89, 517–527 (1978) (34).

As described above, the expression of AaIT by an insect virus reduces the time needed to incapacitate a larva. In turn, the maturation and secretion of functional toxin is facilitated by a signal peptide.

An example of a codon optimized DNA sequence encoding a heterologous cuticle signal sequence joined to a codon optimized DNA sequence encoding AaIT and inserted into a baculovirus transfer vector is the transfer vector designated pAC0055.1 (see Examples 1, 2 and 4 below). Samples of an *E. coli* strain HB101 harboring this transfer vector pAC0055.1 were deposited by applicants on December 17, 1992 with the American Type Culture Collection, 12301 Parklawn Drive, Rockville, Md. 20852, U.S.A., and have been assigned ATCC accession number 69166. Using this deposited material, one of ordinary skill in the art can substitute a different signal sequence for the cuticle sequence contained in that plasmid.

Specifically, the first step is to construct a synthetic double stranded DNA fragment which has the following features: (i) a 5' terminal Bam HI-compatible cohesive end; (ii) a sequence encoding the ATG start codon and amino acid sequence of the new signal peptide; and (iii) a sequence encompassing the first 19 nucleotides in the top strand of the codon optimized AaIT gene and the first 23 nucleotides in the bottom strand. The 3' terminus of such a fragment contains a Sal I-compatible cohesive end. Substitution of this fragment for the corresponding Bam HI/Sal I fragment of pAC0055.1 is achieved by joining the following three fragments in the presence of DNA ligase: (1) the Bam HI/Sal I synthetic fragment described above; (2) a Sal I/Kpn I fragment extending from the Sal I site at codons 6–7 in the codon optimized AaIT toxin gene to the Kpn I site in the 3' flanking polyhedrin gene sequence; and (3) the largest Kpn I/Bam HI fragment contained in pAC0055.1. This fragment, which is derived from pVL985 (35), contains the pUC8 cloning vector and AcMNPV sequences which flank the 5' and 3' termini of the polyhedrin gene. Those skilled in the art will recognize that the resulting construct differs from pAC0055.1 only in the nature of the signal peptide.

Once recombinant viruses are prepared containing the codon optimized gene (see discussion above and Examples 1, 2, 4 and 5 below), they are tested to confirm the presence of the codon optimized AaIT gene. Because the codon optimized gene replaces the baculovirus polyhedrin gene, the recombinant viruses which carry the toxin gene are unable to form polyhedra and thus produce occlusion-negative plaques. Plaque purification is used to isolate recombinant viruses containing the AaIT gene from the transfection supernatant by the method of Summers and Smith (12) (see Example 5).

Next, virus infected cells are assayed by dot blot hybridization for nucleic acids that hybridize to a radiolabelled DNA probe specific for the AaIT gene. Radioactivity is detected by autoradiography; a positive result confirms the presence of the AaIT gene in a virus isolate (see Example 6).

Methods similar to those described in Examples 1, 2, 4 and 5 below are used to construct a baculovirus transfer vector containing the native AaIT gene and the native nucleic acid sequence encoding the native AaIT signal sequence, and then to prepare recombinant virus therefrom (see Examples 3–5 below). Polymerase chain reaction is used to verify that the recombinant viruses contain an insert of the correct size containing the AaIT gene (see Example 7 below). The recombinant viruses containing the native AaIT gene are used as positive controls in assays for the biological activity of recombinant viruses containing the codon optimized AaIT gene with heterologous signal sequences.

Expression of the AaIT gene in insect cells infected with either the codon optimized or native AaIT-viruses is estimated by Northern blot analysis of total cellular RNA isolated from virus-infected cells (see Example 8 below). Analysis shows high levels of toxin-encoding RNA 24 hours post-infection (see Example 8 data).

As mentioned above, the baculoviruses infect a wide range of insects, but are not harmful to mammals. All species of insects examined are susceptible to paralysis caused by AaIT; however, mammals are not adversely affected by the toxin.

The comparative biological activity of a wild-type baculovirus, a virus containing the native AaIT gene, and a virus containing the codon optimized AaIT gene (which may also contain a heterologous signal sequence) is assayed by two types of in vivo tests with insect larvae: an injection assay and a feeding assay.

In a preliminary assay, the culture medium and cell pellets (resuspended in buffer solution) obtained during the preparation of codon optimized AaIT-viral stocks are injected into *Musca domestica* (common house fly) larvae to determine whether those samples contain a detectable amount of biologically active AaIT.

Larvae are examined five seconds after injection for evidence of involuntary contraction of body segments. Results from the assay (see Table in Example 9 below) show that biologically active AaIT is detected in the cultured cells infected with 13 of 14 codon optimized AaIT-virus isolates with heterologous signal sequences (esterase-6, adipokinetic hormone and cuticle). The negative results are expected with the IL2-AaIT-virus constructs due to the presence of a frame shift mutation in the toxin gene coding region. The lack of detectable AaIT activity in any of the cell culture supernatants indicates that the level of biologically active secreted toxin is less than about 0.2 µg/ml.

A dose-response injection assay demonstrates that the insertion of the codon optimized AaIT gene enhances the performance of a baculovirus by reducing the time needed to kill a target insect species. As shown in Example 10 below and FIG. 5, budded virus prepared from the codon optimized Cuticle-AaIT-AcMNPV construct and from the wild-type E2 strain of AcMNPV without the AaIT gene are injected into separate groups of mid-fourth instar larvae at doses of $10^2$, $10^3$ and $10^4$ PFU per larva.

At each of the doses tested, the Cuticle-AaIT-AcMNPV kills its host faster than the wild-type AcMNPV. At $10^4$ PFU, the $LT_{50}$ for the wild-type virus is approximately 97 hours, whereas the corresponding $LT_{50}$ for the Cuticle-AaIT AcMNPV is 67 hours. This result shows that insertion of the AaIT gene and the cuticle signal sequence into AcMNPV accelerates the speed of kill through the expression of biologically active toxin.

The injection assay protocol is repeated using older larvae (early fifth instar) with seven different codon optimized heterologous signal-AaIT-AcMNPV constructs, a native AaIT signal-native AaIT gene-AcMNPV construct and a wild-type E2 strain of ACMNPV without the AaIT gene. A dosage of $10^4$ PFU of budded virus of each construct is injected into separate groups of larvae.

As described in Example 11 below, each of the codon optimized heterologous signal-AaIT-AcMNPV constructs (as well as the native AaIT signal-native AaIT gene-AcMNPV construct) kills its host faster than the wild-type AcMNPV. The $LT_{50}$ for the wild-type virus is approximately 126 hours, whereas the corresponding $LT_{50}$ for the seven heterologous signal-AaIT-AcMNPV constructs range from approximately 68–89 hours, and the native AaIT-AcMNPV construct has an $LT_{50}$ of approximately 74 hours. These results confirm the results of Example 10 that insertion of the AaIT gene and a heterologous signal sequence into AcMNPV accelerates the speed of kill through the expression of biologically active toxin.

In order to test the oral toxicity of these recombinant viruses, which are defective for the production of polyhedrin, polyhedra containing a mixture of wild-type and recombinant virions are prepared by co-infecting cells in culture with the recombinant AaIT-virus and a wild-type helper virus (such as the E2 strain of AcMNPV). This approach is made possible because one polyhedron (occlusion body) contains several hundred virions.

Accordingly, host cells are co-infected with various amounts of the recombinant AaIT-virus, as well as a wild-type virus. The resulting infected cells have polyhedra containing a mixture of wild-type and recombinant virions. As seen in Example 12 below, when the MOI of the wild-type virus is at least 2 PFU per cell, as the MOI of the recombinant virus increases, the percent of cells with viral occlusions and the average number of polyhedra per cell decrease significantly. Therefore, further co-occlusion studies are conducted with the occlusion-negative recombinant virus and the wild-type virus, each at an MOI of 3. This allows effective representation of the recombinant virions in the polyhedra at an acceptable level of polyhedron production.

Finally, an oral toxicity assay is conducted by feeding larvae a microdrop of insect diet containing a desired amount of PIBs. With the exception of the wild-type virus, each PIB contains a mixture of wild-type virus and recombinant virions. The recombinant virions may encode either the native AaIT gene (and native signal sequence), or the codon optimized gene linked to a heterologous signal sequence.

Larvae are then monitored for paralysis and death. The results of the assay are set forth in Example 13 and FIGS. 6–15.

All but one of the recombinant viruses demonstrate an earlier onset of morbidity than the wild-type AcMNPV (which lacks the AaIT gene). The exception is the AcMNPV construct containing the pBMHPC-12 signal sequence linked to the codon optimized sequence encoding AaIT, which performs approximately the same as the wild-type AcMNPV. The recombinant viruses exhibit a characteristic paralytic response which is easily distinguished from the pathogenesis caused by the wild-type viruses. The actual ratio of wild-type to recombinant virus in the polyhedra and in the infected insects is not analyzed.

The present invention further comprises DNA sequences which, by virtue of the redundancy of the genetic code, are biologically equivalent to the native or codon optimized sequences described specifically herein which encode for the signal sequences, that is, these other DNA sequences (including the native DNA sequences) are characterized by nucleotide sequences which differ from those set forth herein, but which encode a signal sequence having the same amino acid sequences as those encoded by the codon optimized DNA sequences set forth herein.

In particular, the invention contemplates those DNA sequences encoding the heterologous signal sequences and/or AaIT which are sufficiently duplicative of the sequences of SEQ ID NOS. 1, 3, 5, 7, 9, 11, 13, 15, 17, 19, 21, 23, 25, 27, 29 and 31 so as to permit hybridization therewith under standard high stringency Southern hybridization conditions, such as those described in Sambrook et al. (36), as well as the biologically active signal sequences produced thereby.

This invention also comprises DNA sequences which encode amino acid sequences which differ from those of the described signal sequences, but which are the biological equivalent to those described for the signal sequences. Such amino acid sequences may be said to be biologically equivalent to those of the signal sequences if their sequences differ only by minor deletions from or conservative substitutions to the signal sequences, such that the tertiary configurations of the sequences are essentially unchanged from those of the signal sequence.

For example, a codon for the amino acid alanine, a hydrophobic amino acid, may be substituted by a codon encoding another less hydrophobic residue, such as valine, leucine or isoleucine. Similarly, changes which result in substitution of one negatively charged residue for another, such as aspartic acid for glutamic acid, or one positively charged residue for another, such as lysine for arginine, as well as changes based on similarities of residues in their hydropathic index, can also be expected to produce a biologically equivalent product. Nucleotide changes which result in alteration of the N-terminal or C-terminal portions of the molecule would also not be expected to alter the activity of the signal sequence. It may also be desirable to eliminate one or more of the cysteines present in the sequence, as the presence of cysteines may result in the undesirable formation of multimers when the protein is produced recombinantly, thereby complicating the purification and crystallization processes. Each of the proposed modifications is well within the routine skill in the art, as is determination of retention of activity of the encoded signal sequences. Therefore, where the terms "signal sequence gene", "DNA encoding signal sequence" and "signal sequence" are used in either the specification or the claims, each will be understood to encompass all such modifications and variations which result in the production of a biologically equivalent signal sequence.

In order that this invention may be better understood, the following examples are set forth. The examples are for the purpose of illustration only and are not to be construed as limiting the scope of the invention.

EXAMPLES

Standard molecular biology techniques are utilized according to the protocols described in Sambrook et al. (36).

EXAMPLE 1

Determination of a Codon Optimized cDNA Sequence Encoding AaIT

The design of a codon optimized gene for AaIT begins with an attempt to reflect the codon usages of nuclear genes derived from the exact (or as closely related as possible) genome of the cell/organism that is intended to be used for recombinant protein expression. Here, however, adequate representation for both lepidopteran and baculoviral gene sequences was not available to create a reliable codon usage table for these initial experiments.

Ikemura et al. have cautioned that reliable codon-choice patterns require the summation of codon frequencies from ten or more genes with varying functions (16,28). However, at the time of this invention, there was DNA sequence information from only two specialized proteins: AcMNPV polyhedrin and AcMNPV p10 (37,38).

For this reason, *Drosophila melanogaster* is selected because its codon use tables are derived from 44 nuclear genes totalling 20,451 codons (17). These codon use tables are used to design the codon optimized genes encoding signal sequences and the AaIT toxin sequence of this invention.

Each full length signal peptide sequence is fused to the AaIT toxin peptide sequence. These amino acid sequences are reverse-translated into a DNA sequence showing all possible nucleotide degeneracies (maximum ambiguity) using IntelliGenetics Suite™ software (version 1988; Palo Alto, Calif.). IntelliGenetics Suite™ software is used for all computer-assisted nucleic acid sequence analysis.

A list of definite and potential (because of codon degeneracies) restriction enzyme recognition sites is generated. Restriction enzyme sites critical for gene synthesis as well as for the convenience of additional DNA manipulation are selected and preserved. For example, Bam HI and Ava I restriction enzyme sites are required for gene synthesis using Bluescript SK/KS vectors (Stratagene, LaJolla, Calif.). Sal I and Apa I restriction sites are desirable to permit flexibility for additional gene manipulation.

Using IntelliGenetics Suite™ software, a list recording the number of times each amino acid occurs in AaIT and each signal sequence is generated. Codons are assigned on the basis of the number of amino acid residues present in the sequence to reflect the relative frequency of *Drosophila melanogaster* codon use (17).

For example, the cysteine codon frequency in *Drosophila melanogaster* is 76% for the sequence TGC and 24% for the sequence TGT. There are eight cysteine residues in the ADK signal-AaIT gene construct (all in the gene coding for the mature AaIT protein (SEQ ID NO: 31)). Hence, six codons are allocated as TGC (75% of the residues) and two codons as TGT (25% of the residues). Based on this distribution, each cysteine codon is then assigned an exact, unambiguous sequence. Attention is given to alternating adjacent isocodons. For example, the two adjacent cysteine residues in the AaIT peptide (amino acids 37 and 38) are assigned the sequence TGC TGC to avoid assigning two identical codon sequnces sequentially.

This process is repeated for all twenty amino acids and the termination codon (although the termination codon sequence TAA is not changed by this procedure). In addition, all critical restriction enzyme sites are preserved and unwanted sites are destroyed.

Flanking DNA sequences for the plasmid vectors as well as the transfer vectors are fused to the completed gene sequences to confirm that there are no undesirable restriction enzyme sites at the splice-junction boundaries.

EXAMPLE 2

Construction of Gene Cassettes Containing an Heterologous Signal Sequence Plus the Codon Optimized cDNA Sequence Encoding AaIT Eight heterologous signal sequence-codon optimized AaIT toxin gene cassettes are synthesized and assembled in two pieces: A "B" fragment, unique for each construct, consisting of DNA coding for one of eight heterologous signal sequences, plus the amino terminal portion of the toxin coding region (common to all constructs), and an "A" fragment, which is the same for each construct and encodes the remainder of the toxin coding region.

Each of fragments A and B is made by annealing a pair of oligomers containing a 15 bp overlap purchased from New England Biolabs (Beverly, Mass.). Sequenase™ 2.0, a DNA polymerase (United States Biochemical Corporation, Cleveland, Ohio), is used to complete the double stranded molecule, which contains the heterologous signal sequence plus the codon optimized cDNA sequence encoding AaIT. The following is a list of the oligomers used in the construction of these eight constructs:

| | | Fragment A | | |
|---|---|---|---|---|
| E1 | 5' AGCCCCCGAG | TGCCTGCTCT | CGAACTATTG | |
| | CAACAATGAA | TGCACCAAGG | TGCACTACGC | |
| | TGACAAGGGC | TACTGTTGCC | TTCTGTCCTG | |
| | CTATTGCTTC | 3' | (SEQ ID NO: 33) | |
| E2 | 5' CTGTAGGTAC | CGGATCCTTA | GTTAATGATG | |
| | GTGGTGTCAC | AGTAGCTCTT | GCGAGTATCA | |
| | GAGATTTCCA | GAACTTTCTT | GTCGTCGTTG | |
| | AGACCGAAGC | AATAGCAGGA | 3' | |
| | (SEQ ID NO: 34) | | | |
| | | Fragments B1–8 | | |
| Common | 5' AGGCACTCGG | GGGCTTTTCC | GGATGAGGTC | |
| | GACTGCGTAG | CCGTTCTTCT | T | 3' |
| | (SEQ ID NO: 35) | | | |
| IL-2 | 5' CCCCCCGGAT | CCATGTACCG | CATGCAGCTG | |
| | CTCTCCTGCA | TCGCCCTGTC | GCTGGCTCTG | |
| | GTGACCAATA | GCAAGAAGAA | CGGCTAC | 3' |
| | (SEQ ID NO: 36) | | | |
| ADK | 5' CCCCCCGGAT | CCATGTACAA | ACTGACCGTC | |
| | TTCCTGATGT | TCATCGCCTT | CGTGATTATC | |
| | GCTGAGGCCA | AGAAGAACGG | CTAC | 3' |
| | (SEQ ID NO: 37) | | | |
| Chorion | 5' CCCCCCGGAT | CCATGTTCAC | CTTCGCTATT | |
| | CTGCTCCTGT | GCGTGCAAGG | CTGCCTGATC | |
| | CAGAATGTTT | ACGGAAAGAA | GAACGGCTAC | 3' |
| | (SEQ ID NO: 38) | | | |
| Esterase-6 | 5' CCCCCCGGAT | CCATGAACTA | CGTCGGGCTG | |
| | GGCCTCATCA | TTGTGCTGTC | GTGCTTGTGG | |
| | CTGGGGAGCA | ATGCTAAGAA | GAACGGCTAC | 3' |
| | (SEQ ID NO: 39) | | | |
| Apolipophorin | 5' CCCCCCGGAT | CCATGGCCGC | TAAATTCGTC | |
| | GTGGTTCTGG | CCGCTTGCGT | CGCCCTGAGC | |
| | CACTCGGCTA | TGGTGCGCCG | CAAGAAGAAC | |
| | GGCTAC | 3' | | |
| | (SEQ ID NO: 40) | | | |
| Sex-Specific | 5' CCCCCCGGAT | CCATGCGCGT | CCTGGTGCTG | |

-continued

|  |  |  |  |  |
|---|---|---|---|---|
|  | TTGGCCTGCC | TGGCAGCCGC | TAGCGCTAAG |  |
|  | AAGAACGGCT | AC | 3' | (SEQ ID NO: 41) |
| Cuticle | 5' CCCCCCGGAT | CCATGTTCAA | GTTCGTGATG |  |
|  | ATCTGCGCCG | TCCTCGGCCT | GGCTGTGGCC |  |
|  | AAGAAGAACG | GCTAC | 3' | (SEQ ID NO: 42) |
| pBMHPC-12 | 5' CCCCCCGGAT | CCATGAAACT | CCTGGTCGTG |  |
|  | TTCGCCATGT | GCGTGCCCGC | TGCCAGCGCT |  |
|  | AAGAAGAACG | GCTAC | 3' | (SEQ ID NO: 43) |

FIG. 2 depicts the construction strategy for the AaIT gene cassette which contains the *Drosophila melanogaster* cuticle signal sequence. The remaining seven heterologous signal sequence-AaIT gene cassettes are constructed in the same way using the specific oligo for the signal sequence as indicated above.

In the first step, the signal sequence-specific oligo for the B fragment and the common B oligo are annealed and the single stranded regions are filled in using Sequenase™ 2.0. Each signal sequence-specific oligo consists of an identical 12 nucleotide upstream noncoding region containing the Bam HI site required for cloning, the coding region for the signal sequence, and the first 15 nucleotides encoding the first five amino-terminal amino acids of AaIT. This short piece of double stranded DNA is digested with Bam HI and Ava I and subcloned into pBluescript SK+ (Stratagene, LaJolla, Calif.) which had been digested with Xma I and Bam HI. Positive subclones are verified by the presence of a Pvu II fragment larger than the 445 bp fragment present in pBluescript SK+ alone. There is a single base pair mismatch between the overhangs for the Ava I and Xma I sites. Clones which have corrected this mismatch to regenerate the Ava I site and lôse the Xma I site are selected by the appropriate restriction enzyme digestions. In FIG. 2, the resulting plasmid is designated pBS Cuticle B7.

To construct the A fragment encoding the bulk of the AaIT coding region, oligos E1 and E2 are annealed and Sequenase™ 2.0 is used to fill in the single stranded regions. This results in a double stranded molecule which contains an Ava I site at the 5' terminus and nested Bam HI and Asp 718 sites following the 3' end of the toxin coding region. The Bam HI and Asp 718 sites are introduced in order to facilitate cloning. Fragment A is then digested with Ava I and Asp 718. The fragment B-containing plasmid, pBS Cuticle B7, is also digested with Ava I and Asp 718 and Fragment A is subcloned into the digested plasmid. In the case of FIG. 2, the resulting plasmid is designated pBS Cuticle-AaIT. Fragments A and B are joined at a unique Ava I site which is engineered into the AaIT sequence just for this purpose. After the ligation of fragment A into the fragment B-containing plasmid, the ligated DNA is used to transform competent DHα *E. coli.* Minipreps of plasmid DNA are prepared from the resulting bacterial colonies. Restriction enzyme analysis is used to determine which colonies contain the desired recombinant DNA. Further restriction enzyme analysis, followed by DNA sequencing, is used to confirm the integrity of the eight plasmids containing the codon optimized cDNA encoding AaIT.

EXAMPLE 3

Construction of Gene Cassette Containing the Native cDNA Sequence Encoding AaIT A gene cassette containing the native cDNA sequence encoding AaIT is constructed in two pieces, but in a manner different from the construction of the codon optimized genes of Example 2. Instead of using long oligos which have only a short region of overlap to construct the gene, sets of oligos which completely overlap are used. A second difference in the manner of construction is necessitated because the native DNA sequences for both the AaIT signal sequence and coding region are used. No artificial restriction enzyme sites are engineered into the DNA sequence. Therefore, a different method of joining the signal sequence and coding region of the AaIT gene is required. In this method, asymmetrically cutting restriction enzymes are used to allow functionally separate regions of the gene to be neatly fused to each other. This allows one to mix and match premade regions in any future constructions. The sequences of the oligomers numbered 1–10 used for the construction of the native AaIT gene are provided in the list below:

| | | | |
|---|---|---|---|
| Oligo 1 | GATCCGATGA | AATTTCTCCT | ATTGTTTCTC |
| | GTAGTCCTTC | CAATAATGGG | GGTGCTTGGC |
| | (SEQ ID NO: 44) | | |
| Oligo 2 | GCCAAGCACC | CCCATTATTG | GAAGGACTAC |
| | GAGAAACAAT | AGGAGAAATT | TCATCG |
| | (SEQ ID NO: 45) | | |
| Oligo 3 | AAGAAGAATG | GATATGCCGT | CGATAGTAGT |
| | GGTAAAGCTC | (SEQ ID NO: 46) | |
| Oligo 4 | CTCAAAAGAC | ATTCAGGAGC | TTTACCACTA |
| | CTATCGACGG | CATATCCATT | CTTCTT |
| | (SEQ ID NO: 47) | | |
| Oligo 5 | CTGAATGTCT | TTTGAGCAAT | TACTGTAACA |
| | ACGAATGCAC | AAAAGTACAT | TATGCT |
| | (SEQ ID NO: 48) | | |
| Oligo 6 | CAGCAATATC | CTTTGTCAGC | ATAATGTACT |
| | TTTGTGCATT | CGTTGTTACA | GTAATTG |
| | (SEQ ID NO: 49) | | |
| Oligo 7 | GACAAAGGAT | ATTGCTGCTT | ACTTTCATGT |
| | TATTGCTTCG | GTCTAAATGA | CGATAAAAAA |
| | GTTTTG | (SEQ ID NO: 50) | |
| Oligo 8 | CTTGTGTCCG | AAATCTCCAA | AACTTTTTTA |
| | TCGTCATTTA | GACCGAAGCA | ATAACATGAA |
| | AGTAAG | (SEQ ID NO: 51) | |
| Oligo 9 | GAGATTTCGG | ACACAAGGAA | AAGTTATTGT |
| | GACACCACAA | TAATTAATTA | AG |
| | (SEQ ID NO: 52) | | |
| Oligo 10 | AATTCTTAAT | TAATTATTGT | GGTGTCACAA |
| | TAACTTTTC | (SEQ ID NO: 53) | |

In order to facilitate the cloning of the native AaIT toxin gene cassette, a modified Bluescript SK plasmid is generated. This vector designated pBS SK Bsm I has a Bgl II linker (CAGATCTG) inserted into the Nae I site located at 330 bp on the Bluescript map. This linker insertion destroys the Nae I site. In addition, this vector contains a modified polylinker as shown at the top in FIG. 3. This modified plasmid is designated pBS SK Bsm I. This polylinker contains a Nae I site located adjacent to a Bsm I site, such that any sequence cloned into the Nae I site can be cleanly excised as a blunt-ended molecule by using the Bsm I restriction enzyme followed by filling in of the sticky end with the Klenow fragment of DNA polymerase I (Gibco/BRL, Gaithersburg, Md.).

To construct the native signal sequence portion of the cassette, oligos 1 and 2 are annealed. When these two oligos are properly annealed, they contain a blunt 3' end and a Bam HI sticky end at the 5' terminus. The plasmid pBS SK Bsm I is digested with Bam HI and Nae I. The annealed oligos are then ligated to the digested plasmid. The resulting plasmid subclone is designated pBS GIII sig.

Figure 3:
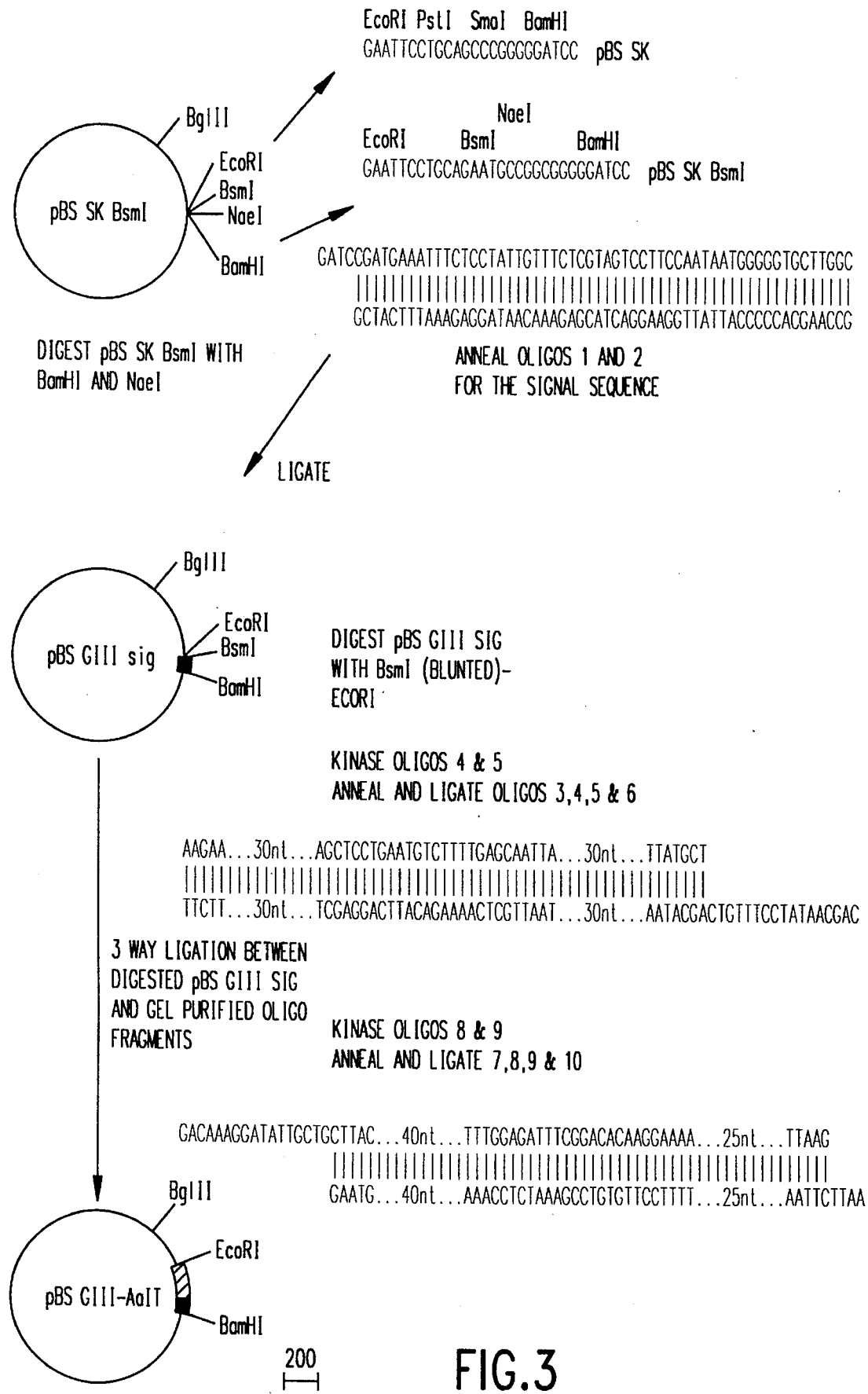

The coding region of the AaIT toxin is constructed as two pieces of DNA. The 5' ends of oligos 4, 5, 8 and 9 are phosphorylated using T4 kinase. Oligos 3, 6, 7 and 10 are left without a terminal phosphate. Two annealing reactions, followed by a ligation reaction using T4 DNA ligase (New England Biolabs, Beverly, Mass.) are carried out. Oligos 3, 4, 5, and 6, which encode the amino terminal portion of the AaIT toxin, are annealed and ligated as shown in FIG. 3. Oligos 7, 8, 9 and 10, which encode the carboxy terminus of the AaIT toxin, are annealed and ligated as shown in FIG. 3.

These two oligo fragments are purified by electrophoresis on a 2.5% low melt agarose gel (BioRad, Richmond, Calif.) containing TAE (40 mM Tris-acetate, pH 7.8, 1 mM EDTA). When the fragments are sufficiently separated from contaminating fragments, they are cut out as gel slices and placed in individual tubes. The fragments are purified by phenol extraction as described in Sambrook et al. (36) with the following modifications: (1) Sodium chloride is added to the gel slices to a final concentration of 1.5M prior to heating. No further addition of salt is required in the subsequent steps. (2) Only two phenol extractions are performed on the liquified and diluted gel slice prior to the ethanol precipitation.

The plasmid pBS GIII sig is digested with Bsm I and the sticky end is filled in and blunted with the Klenow fragment of DNA polymerase I (BRL). As described above, this results in opening the plasmid at the last base pair of the signal sequence. The plasmid is then further digested with Eco RI. A three way ligation is then set up between the gel purified oligo fragments and the digested plasmid. Positive subclones are verified by restriction enzyme analysis, followed by DNA sequencing. One positive clone designated pBS GIII-AaIT contains the native signal sequence and full length native coding region of AaIT (FIG. 3).

EXAMPLE 4

Insertion of AaIT Gene Constructs into Baculovirus Transfer Vectors

The heterologous signal sequence-codon optimized AaIT gene cassettes of Example 2 are isolated as Bam HI fragments from the pBS signal-AaIT clones (see pBS Cuticle-AaIT example in FIG. 2. These Bam HI fragments are subcloned into the pVL 985 baculovirus transfer vector DNA (35) which had been digested with Bam HI. Restriction enzyme analysis followed by sequencing of the insert is used to confirm the correct orientation and integrity of the pVL heterologous signal sequence-codon optimized AaIT clones.

For example, the plasmid pBS Cuticle-AaIT is subcloned into the pVL bacutovirus transfer vector to yield the plasmid designated pAC0055.1.

The native AaIT gene cassette of Example 3 is isolated as a Bam HI to Eco RI fragment from the pBS GIII-AaIT clone (see FIG. 3). These Bam HI to Eco RI fragments are subcloned into pVL 1393 baculovirus transfer vector DNA (39) which had been digested with Bam HI and Eco RI. Restriction enzyme analysis followed by sequencing of the insert is used to confirm the integrity of the pVL native AaIT clones.

EXAMPLE 5

Generation of Recombinant Viruses Encoding AaIT

Recombinant viruses containing the native and codon optimized AaIT genes under the control of the AcMNPV polyhedrin promoter are generated by homologous DNA recombination in cultured Sf9 cells, as described by M. D. Summers and G. E. Smith (12). Sf9 cells (ATCC accession number CRL1711) are derivatives of the cell line designated *Spodoptera frugiperda* 21 (Sf21).

In this procedure, $2.0 \times 10^6$ Sf9 cells are seeded in a 60 mm culture dish in 5 ml of supplemented TNM-FH medium (Grace's insect medium (40) supplemented with 0.33% TC lactalbumin hydrolysate (Difco, Detroit, Mich.) and 0.33% TC yeastolate (Difco), 10% fetal bovine serum, 0.1% Pluronic™ F-68 (Gibco/BRL)). Once the cells are firmly attached (2–16 hours), the medium is removed and replaced with 0.75 ml of Grace's insect medium supplemented with 10% fetal bovine serum. One microgram of AcMNPV (E2 strain) DNA is mixed with 2 μg of AaIT-transfer vector DNA from Example 4 in 0.75 ml of transfection buffer (25 mM HEPES, pH 7.05, 140 mM NaCl, 125 mM $CaCl_2$) and added dropwise to the cells. The cells are then incubated at 27° C. for 4 hours. At the end of the incubation period, the transfection medium is removed and the cells are washed once with TNM-FH, fed again with 5 ml of supplemented TNM-FH, and placed in a 27° C. incubator. After five days, the medium is removed from the cells, clarified by centrifugation for 10 minutes at 2000 rpm in a Beckman GPR centrifuge, and stored at 4° C. This constitutes the primary transfection supernatant.

Because the native and codon optimized AaIT genes replace the AcMNPV polyhedrin gene, the recombinant viruses which carry these toxin genes are unable to form polyhedra and, therefore, give rise to occlusion-negative plaques. Using this phenotype as a basis for identification, recombinant viruses containing the AaIT genes are isolated from the primary transfection supernatant by three rounds of plaque purification, using the plaque assay method of M. D. Summers and G. E. Smith (12).

In this procedure, $1.5–2.0 \times 10^6$ Sf9 cells are seeded into a 60 mm culture in supplemented TNM-FH. After the cells attach (2–16 hours), the medium is removed and replaced with 1 ml of supplemented TNM-FH containing 0.001–0.1% primary transfection supernatant. The virus is allowed to adsorb to the cells for 1–2 hours at 27° C., after which it is removed and replaced with 4 ml of molten (39° C.) supplemented TNM-FH containing antibiotics and 1.5% low gelling temperature agarose. Once the agarose gels, the cells are transferred to an humidified 27° C. incubator for 4–6 days. Occlusion-negative plaques are then identified by visual inspection under a stereo microscope and an agarose plug overlying each desired plaque is picked and diluted into 1 ml of supplemented TNM-FH.

The plaque purification procedure is repeated two additional times using 1–10% of the total virus recovered from each plaque. At the end of the third round, all of the virus recovered from a single plaque (i.e., 1 ml) is added to $2 \times 10^6$ Sf9 cells seeded in a 25 $cm^2$ flask and the flask is incubated at 27° C. for 1–2 hours. The virus is then removed and replaced with 3 ml of supplemented TNM-FH, and the flask is returned to the incubator. At the end of 5 days, the supernatant, which is designated as the passage 1 or "P1" virus stock, is clarified by centrifugation for 10 minutes at 2000 rpm in a Beckman GPR centrifuge. Archive samples of the P1 stock are kept at −150° C., and the remainder of the virus is stored at 4° C.

Confirmation that the occlusion-negative viruses contain the desired AaIT gene is achieved by dot blot hybridization for the codon optimized AaIT-viruses (Example 6 below) and by polymerase chain reaction (PCR) for the native AaIT-virus (Example 7 below).

EXAMPLE 6

Confirmation of Recombinant Viruses By Dot Blot Hybridization

To confirm the presence of the codon optimized AaIT gene in occlusion-negative viruses, virus-infected Sf9 cells from Example 5 are assayed by dot blot hybridization for nucleic acids that hybridize to a radiolabelled DNA probe specific for the AaIT gene. For this method, the cell pellets obtained during clarification of the viral P1 stocks are each resuspended in 1 ml Dulbecco's Phosphate Buffered Saline (D-PBS) and 100 μl aliquots are removed for hybridization. The cells are pelleted in an Eppendorf centrifuge at maximum speed for 15 seconds and then solubilized in 0.5 ml 0.5M NaOH. After 10 minutes at room temperature, each sample is neutralized with 50 μl of 10M $NH_4OH$. With the aid of a 96 well dot blot apparatus, 10 to 100 μl of the solubilized cell pellet is passed through a 3 mm diameter circle on a nitrocellulose membrane (Schleicher and Schuell BAS5, Keene, N.H.) equilibrated with 1M $NH_4OH$, 0.02M NaOH. The wells of the blot apparatus are then washed with 0.5 ml 1M $NH_4OH$, 0.02M NaOH. The filter is removed from the apparatus, rinsed with 5×SSPE (0.9M NaCl, 50 mM $NaH_2PO_4$, 16.25 mM NaOH, 5 mM EDTA), and the nucleic acids are baked onto the membrane in a vacuum oven at 80° C. for 2–3 hours. Before use, the membrane is incubated overnight at 42° C. in prehybridization buffer (5×SSPE, 50% (v/v) formamide, 0.2% SDS, 5×Denhardt's (0.1% (w/v) polyvinylpyrrolidone, 0.1% (w/v) Ficoll 400™ (Pharmacia LKB, Piscataway, N.J.), 0.1% (w/v) bovine serum albumin)).

The hybridization probe for codon optimized AaIT gene constructs is a $^{32}P$-labeled double-stranded DNA prepared by annealing oligonucleotides E1 and E2 (described in Example 2) and then filling in the single-stranded regions with phage T7 DNA polymerase in the presence of 32P-labeled dATP and unlabelled dCTP, dGTP and TTP. The radiolabelled probe is denatured by heating and then diluted in hybridization buffer (prehybridization buffer supplemented with 100 μg/ml sheared and denatured salmon sperm DNA). The membrane is placed in the probe-containing hybridization buffer and incubated at 37° C. for 16 hours. Unhybridized probe is then removed through four successive 20–30 minute washes: two at room temperature in 2×SSPE, 0.2% SDS, and two at 65° C. in 0.2×SSPE, 0.2% SDS. Excess fluid is removed from the membrane and the membrane-bound radioactivity is detected by autoradiography using Kodak XAR medical X-ray film in the presence of an DuPont Cronex™ (Wilmington, Del.) Lightning Plus intensifying screen. Using this assay, the presence of the AaIT gene is confirmed in 93% of the putative codon optimized AaIT-virus isolates examined.

EXAMPLE 7

Confirmation of Recombinant Viruses Using the Polymerase Chain Reaction (PCR)

To verify that the putative native AaIT recombinant viruses contain an insert of the correct size, the distance between two known marker sites flanking the site of AaIT gene insertion is measured by PCR analysis of budded virus. The procedure is a modification of that described by B. Malitschek and M. Schartl (41). The primers for this analysis are located 84 to 110 bases upstream (5'-CAATATATAGTTGCTGATATCATGGAG-3'; PVLForward) and 205 to 226 bases downstream (5'-GGATTTCCTTGAAGAGAGTGAG-3'; PVLReverse) of the AcMNPV polyhedrin gene translational start site.

To prepare virus samples for analysis, 4 μl aliquots of each P1 stock, and of the wild-type AcMNPV E2 strain as a control, are each mixed in a GeneAmp tube (Perkin-Elmer/Cetus, Norwalk, Conn.) with 21 μl of Buffer A (10 mM Tris-HCl (pH 8.3), 40 mM KCl, 0.1 mg/ml gelatin, 0.45% (v/v) of Nonidet™ P40 (Shell Oil Co.), 0.45% (v/v) Tween™ 20 (ICI Americas) )supplemented with 200 μg/ml of a non-specific protease from *Streptomyces griseus.* Each tube is then incubated in a Perkin-Elmer/Cetus DNA Thermal Cycler running a single cycle three temperature program: (1) 55° C. for 60 minutes, (2) 95° C. for 12 minutes, and (3) soak at 4° C. The function of this program is to liberate the viral DNA from the budded virus and to destroy the pronase prior to the PCR amplification step.

Each sample is prepared for the amplification reaction by adding 24.5 μl of a solution containing 1×Buffer A, 3.0 mM $MgCl_2$, 400 μM dATP, 400 μM dGTP, 400 μM dCTP, 400 μM TTP, 50 pmol primer 1 (PVLForward), 50 pmol primer 2 (PVLReverse). The PCR is initiated by adding 0.5 μl (2.5 units) of AmpliTaq DNA polymerase (Perkin-Elmer/Cetus) and starting a thermal cycler program consisting of 25–35 temperature cycles, wherein each cycle consists of (1) 1 minute at 94° C., (2) 1.5 minutes at 55° C., and (3) 2.5–3.0 minutes at 72° C. On the last cycle, the incubation time at 72° C. is extended an additional 7 minutes, and the samples are then soaked at 4° C. An aliquot of each PCR reaction is then analyzed by gel electrophoresis in the presence of a suitable set of DNA size markers.

Each of four different putative native AaIT recombinant viruses tested by this method yields a single PCR product, the mobility of which is identical among the different samples and commensurate with the predicted size of 493 bp for the fragment being amplified. This fragment contains the primers flanking the site of gene insertion. Similarly, a single PCR product is obtained with the wild-type AcMNPV strain E2 virus, and its mobility is in good agreement with the predicted size of 337 bp.

EXAMPLE 8

Analysis of RNA Levels in Virus-Infected Cells

Expression of the AaIT gene in Sf9 cells infected with the codon optimized and native AaIT-viruses is estimated by Northern blot analysis of total cellular RNA isolated from virus-infected cells. Total cell RNA is isolated by the guanidine thiocyanate/CsCl procedure (42,43).

In this procedure, Sf9 cells ($5\times10^7$ in a 150 $cm^2$ flask) are infected with virus at an MOI of 5 PFU/cell and incubated at 27° C. for 24 hours. The cells are then harvested by centrifugation (2000 rpm for 10 minutes in a Beckman GPR centrifuge) and the cell pellet is resuspended in 10 ml of 4M guanidine thiocyanate solution (50% (w/v) guanidine thiocyanate, 0.5% (w/v) N-laurylsarcosine, 0.7% (v/v) β-mercaptoethanol, 25 mM sodium citrate (pH 7.0)). Total RNA is then partially purified by sedimentation through a 5.7M CsCl, 0.1M EDTA pad in a Beckman 70.1Ti rotor spun at 60,000 rpm for 4.5 hours. The RNA pellet is redissolved in 2 ml TES buffer (10 mM Tris-HCl (pH 7.5), 5 mM EDTA, 1% (w/v) SDS) and incubated for 5–10 minutes at 55° C. to aid dissolution of the sample. The solution is then adjusted to 0.15M NaCl and extracted once with water-saturated phenol. The aqueous phase is removed and the organic phase is re-extracted twice more with 2 ml TES, 0.15M NaCl. The aqueous phases are then combined and the RNA is precipitated with ethanol. The RNA pellet is redissolved in 2 ml $H_2O$ and reprecipitated overnight at 4° C. with an equal volume of 4M LiCl. The pellet is then washed once with ice cold 2M LiCl and redissolved in 0.5 ml $H_2O$. Residual LiCl is then removed by one last ethanol precipitation and the final pellet is redissolved in 0.2 ml $H_2O$. The RNA yield is determined by UV spectroscopy.

For Northern analysis 20 μg of each RNA is size fractionated by electrophoresis on a 1% agarose gel containing 2.7M formaldehyde, 40 mM MOPS (4-morpholinepropane-sulfonic acid)(pH 7.0), 10 mM sodium citrate, 1 mM EDTA. The RNA is then transferred by capillary blotting to a nitrocellulose membrane (Schleicher and Schuell BA85) in the presence of 20×SSC (3M NaCl, 0.3M sodium citrate; adjusted to pH 7.0 with NaOH). The membrane is prehybridized briefly in hybridization buffer (50% (v/v) formamide, 0.9M NaCl, 50 mM sodium phosphate (pH 7.0), 5 mM EDTA, 0.1% (w/v) SDS, 4×Denhardt's, 0.4 mg/ml tRNA, 0.25 mg/ml calf thymus DNA) and then hybridized for 16 hours at 42° C. in the same buffer containing a $^{32}$P-labeled DNA probe prepared by random priming (44) a 464 bp Bam HI to Kpn I restriction fragment lying immediately 3' to the site of AaIT gene insertion in the AcMNPV polyhedrin gene. Following hybridization, unbound probe is removed by four successive 30 minute washes with 0.25×SSC, 0.1% SDS at 65° C. A digitized image of the membrane-bound probe is produced by autoradiography using a Molecular Dynamics PhosphorImager™, and individual bands are quantified using ImageQuant™ v3.15 software (Molecular Dynamics, Sunnyvale, Calif.).

Figure 4:
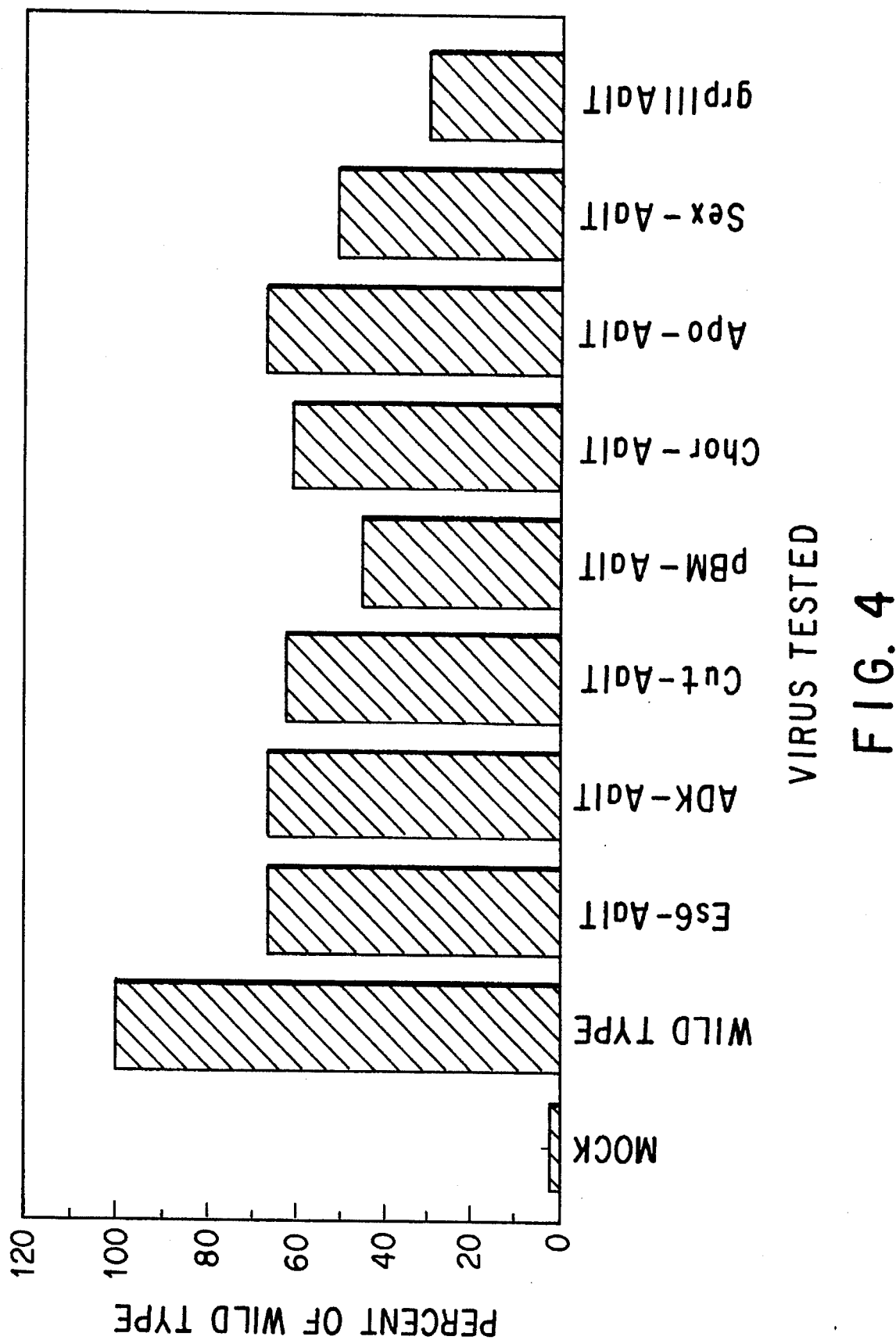

FIG. 4 summarizes an analysis of AaIT/polyhedrin RNA levels in Sf9 cells infected with wild-type AcMNPV (labelled "wild-type") and with the codon optimized (labelled with the specific heterologous signal sequence).and native (labelled grp III AaIT) recombinant viruses. Only one species of polyhedrin-containing RNA is detected in each sample and all are of a size which is appropriate for the structure of the polyhedrin or AaIT/polyhedrin gene present in the virus. The amount of AaIT/polyhedrin RNA detected in the codon optimized AaIT-virus-infected cells ranges from 45–67% of the level of polyhedrin RNA accumulated in wild-type AcMNPV-infected cells. The corresponding value for native AaIT-virus-infected cells is 30%. This analysis shows that the AaIT/polyhedrin gene is correctly utilized and highly active in AaIT-virus-infected Sf9 cells.

EXAMPLE 9

Production of Biologically Active AaIT in Virus-Infected Sf9 Cells

AaIT causes an acute excitatory (contractile) paralysis when 1 ng or more is injected into the dorsolateral area of *Sarcophaga argyrostoma* (flesh fly) larvae (45). A similar assay, using *Musca domestica* (house fly) larvae, is used to determine whether a detectable amount (1 ng) of biologically active AaIT is present in either the culture medium or cell pellets obtained during the preparation of the codon optimized AaIT viral P1 stocks.

To assay the culture medium, 2–6 μl of each P1 stock (600–1000 cell equivalents/μl) are injected into the dorsolateral area of *M. domestica* larvae using a Hamilton syringe equipped with a 26 gauge needle. Larvae are examined five seconds after injection for evidence of involuntary contraction of body segments. Five larvae are assayed for each virus.

To assay AaIT activity in the cell pellets, the virus-infected Sf9 cells are washed once by centrifugation and the resuspended at a density of 30,000 cells per microliter in Dulbecco's phosphate buffered saline (D-PBS). An aliquot of the cell suspension is removed and frozen on dry ice and then thawed at 37° C. three times in quick succession. Two microliters of the freeze/thaw lysate (i.e., 60,000 cell equivalents) are then injected into *M. domestica* larvae as described above and examined for acute contraction of body segments.

The table below summarizes the results obtained with an interleukin-2 signal-AaIT-virus mutant (containing a frame shift mutation) and three other heterologous signal-codon optimized AaIT-virus isolates. Biologically active AaIT cannot be detected in any of the P1 stocks (cell culture supernatants) tested in this assay, indicating that the concentration of active toxin is in the range of 0.2 ng/μl or less in the supernatants. In contrast, AaIT is easily detected in 13 of 17 cell pellet lysates. Three of the four negative lysates are derived from the mutant IL2-AaIT-virus isolates, which contain a frame shift mutation at position 265 in the toxin gene coding region. The other negative is obtained with isolate T9.4.1 (putative Cuticle-AaIT), which is negative by dot blot hybridization for the AaIT gene insert. The other four putative Cuticle-AaIT constructs give positive results, as do all nine of the Esterase-6-AaIT and adipokinetic hormone-AaIT constructs.

| Isolate No. | AaIT Gene | Dot Blot Results | Supernatant | Cell Pellet |
|---|---|---|---|---|
| Mock infected | None | – | 0/5 | 0/5 |
| T6.1.1 | IL2-AaIT | + | 0/5 | 0/5 |
| T6.2.1 | [mutant] | + | 0/5 | 0/5 |
| T6.5.1 | | + | 0/5 | 0/5 |
| T7.2.1 | Es6-AaIT | + | 0/5 | 5/5 |
| T7.3.1 | | + | 0/5 | 5/5 |
| T7.4.1 | | + | 0/5 | 5/5 |
| T7.5.1 | | + | 0/5 | 5/5 |
| T8.1.1 | ADK-AaIT | + | 0/5 | 5/5 |
| T8.2.1 | | + | 0/5 | 5/5 |
| T8.3.1 | | + | 0/5 | 5/5 |
| T8.4.1 | | + | 0/5 | 5/5 |
| T8.5.1 | | + | 0/5 | 5/5 |
| T9.1.1 | Cuticle-AaIT | + | 0/5 | 5/5 |
| T9.2.1 | | + | 0/5 | 5/5 |
| T9.3.1 | | + | 0/5 | 5/5 |
| T9.4.1 | | – | 0/5 | 0/5 |
| T9.5.1 | | + | 0/5 | 5/5 |

EXAMPLE 10

Analysis of Virus Performance by Injection into Larvae

To test whether insertion of the AaIT gene enhances AcMNPV performance, budded virus prepared from the codon optimized Cuticle-AaIT and from the wild-type E2 strain of AcMNPV without the AaIT gene are bioassayed by injection into mid-fourth instar *Heliothis virescens* (tobacco bud worm) larvae. Each virus is titered by the plaque assay method, as described by M. D. Summers and G. E. Smith (12), and then diluted to $2\times10^7$, $2\times10^6$, and $2\times10^5$ PFU/ml in TNM-FH medium supplemented with 0.5% (v/v) red dye number 5. Each larva is anesthetized with carbon dioxide for 2–5 minutes and then injected with 0.5 μl of diluted virus, using a Hamilton syringe equipped with a 26 gauge needle. The needle is inserted longitudinally between the last two prolegs and then moved anteriorly two to three body segments prior to injection. Following injection, each larva is inspected for the release of dye-stained hemolymph and discarded if sample loss is evident or suspected. The larvae are then stored at 27° C. in covered 4 cm² diet cells (one larva per cell) and inspected visually 2–3 times daily for evidence of morbidity or mortality. An individual is scored as moribund (positive response) if it is unable to right itself within 0.5–2 minutes after being turned on its back.

Figure 5A:
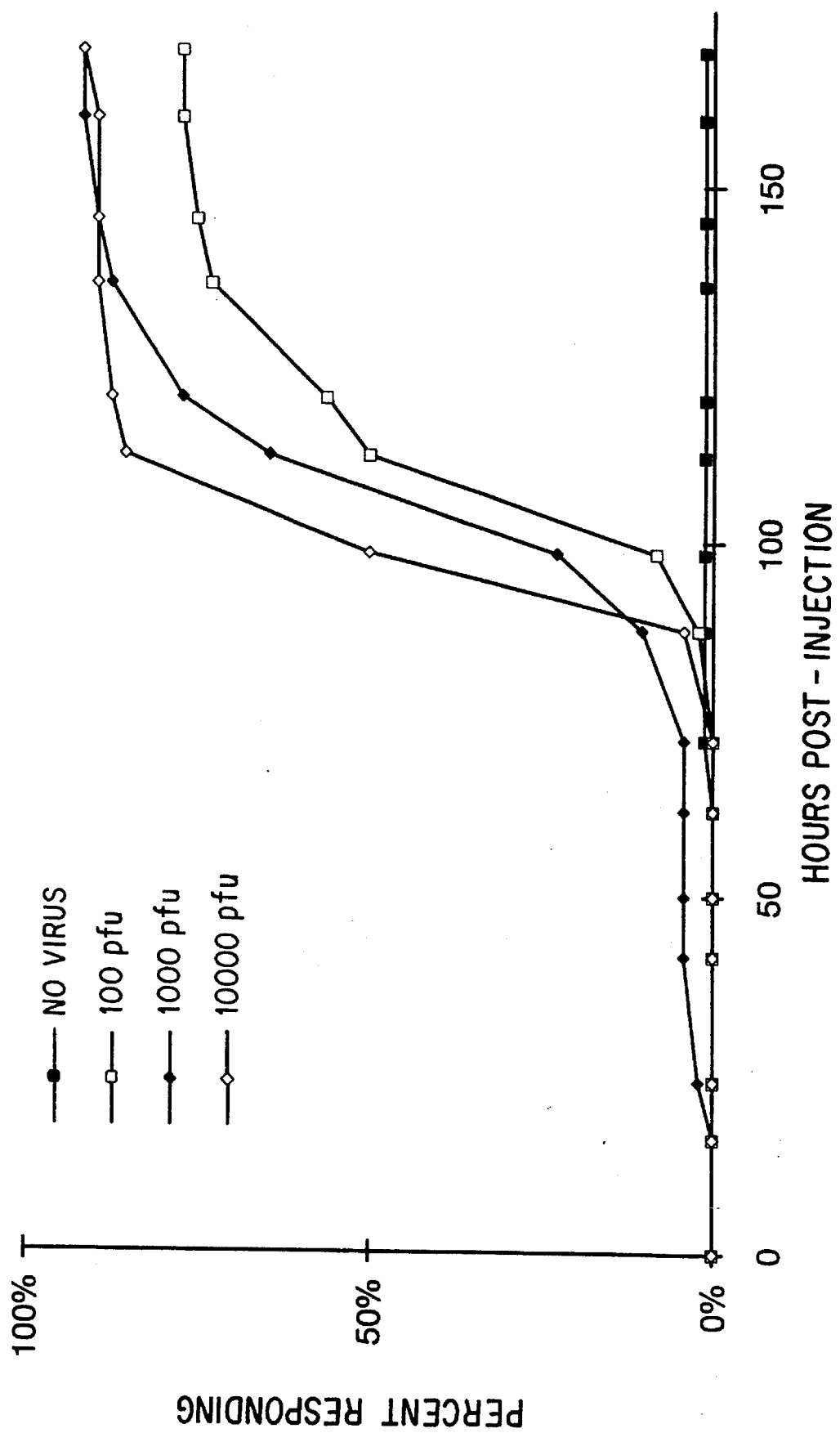
Figure 5B:
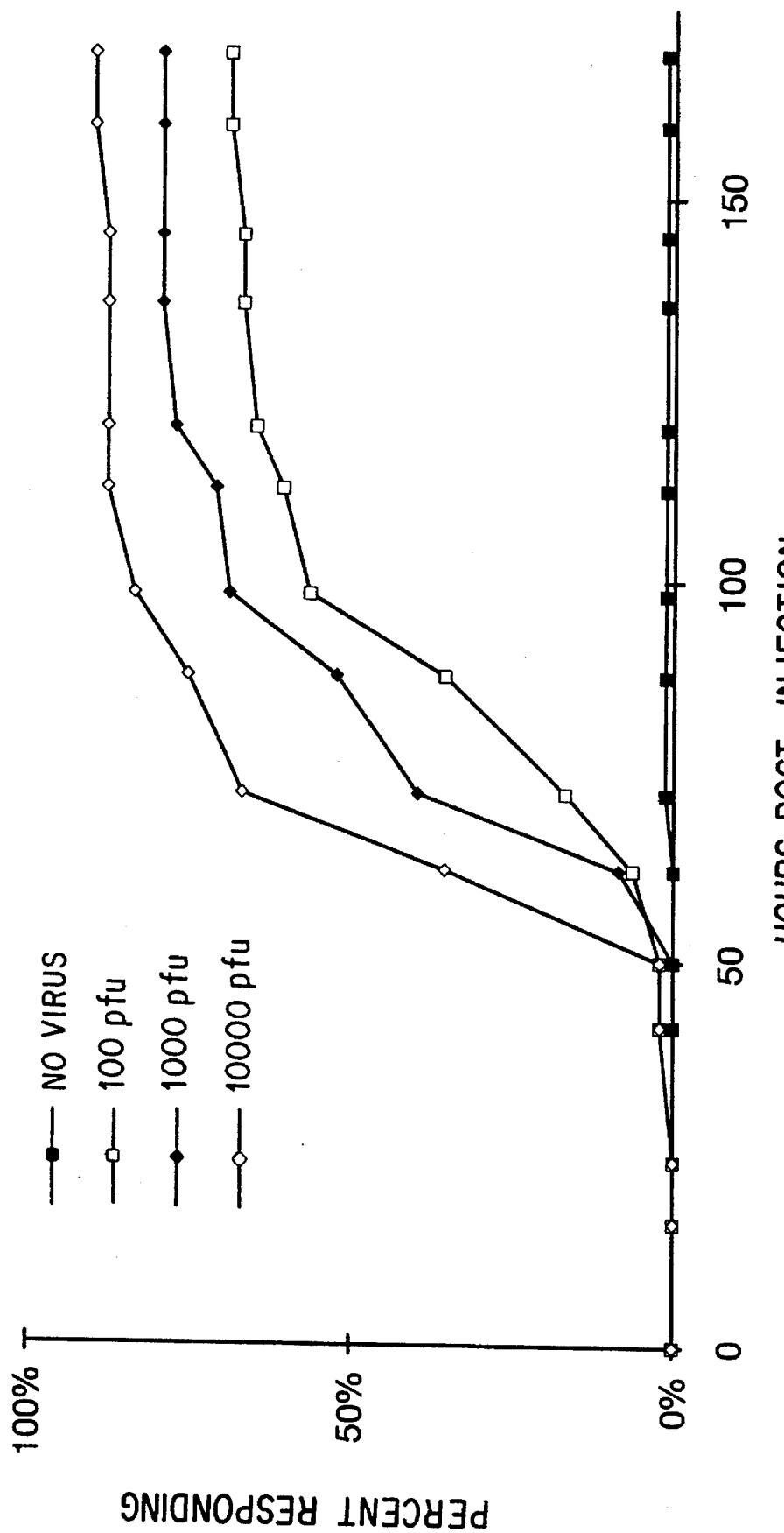
Figure 6:
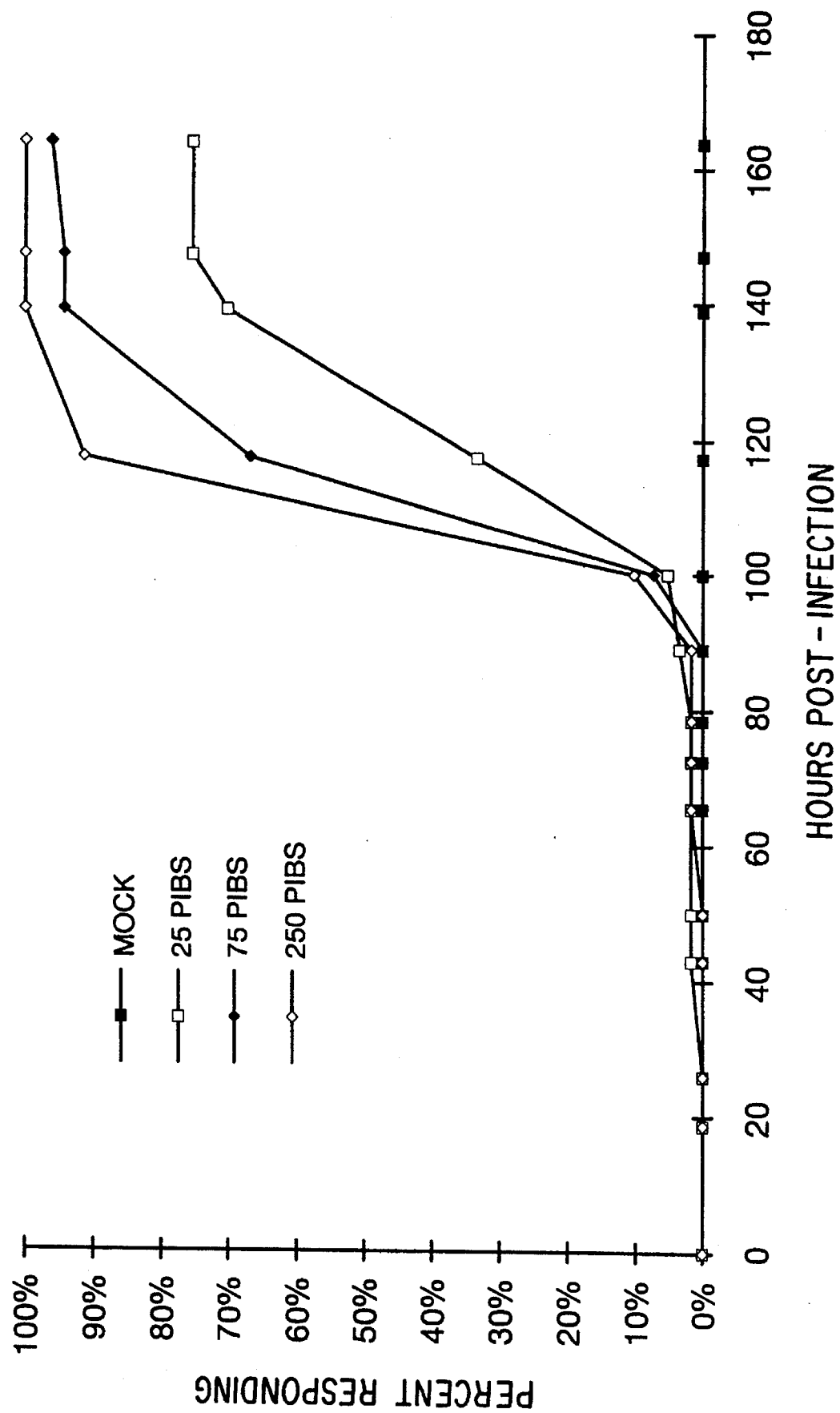
Figure 7:
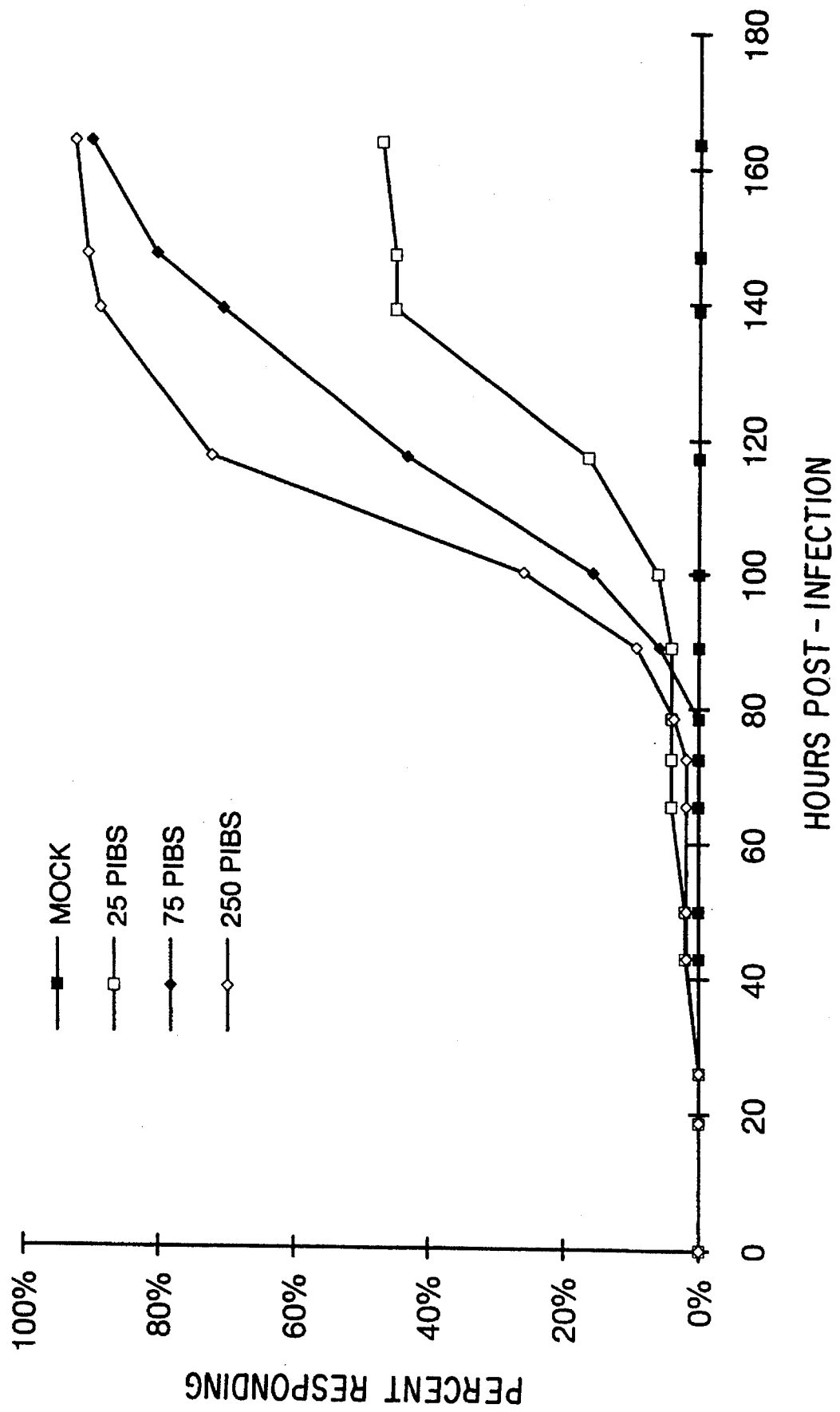
Figure 8:
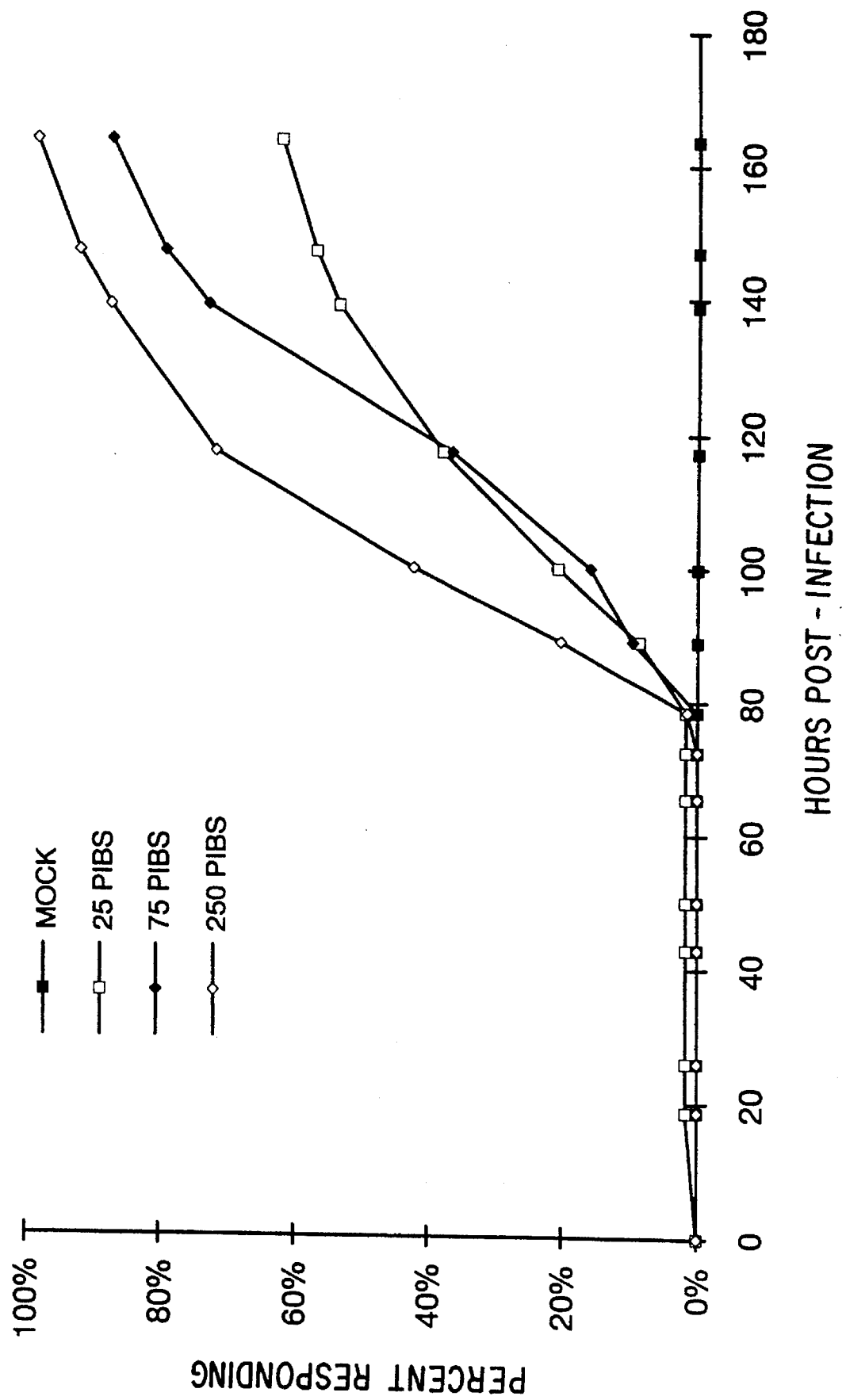
Figure 9:
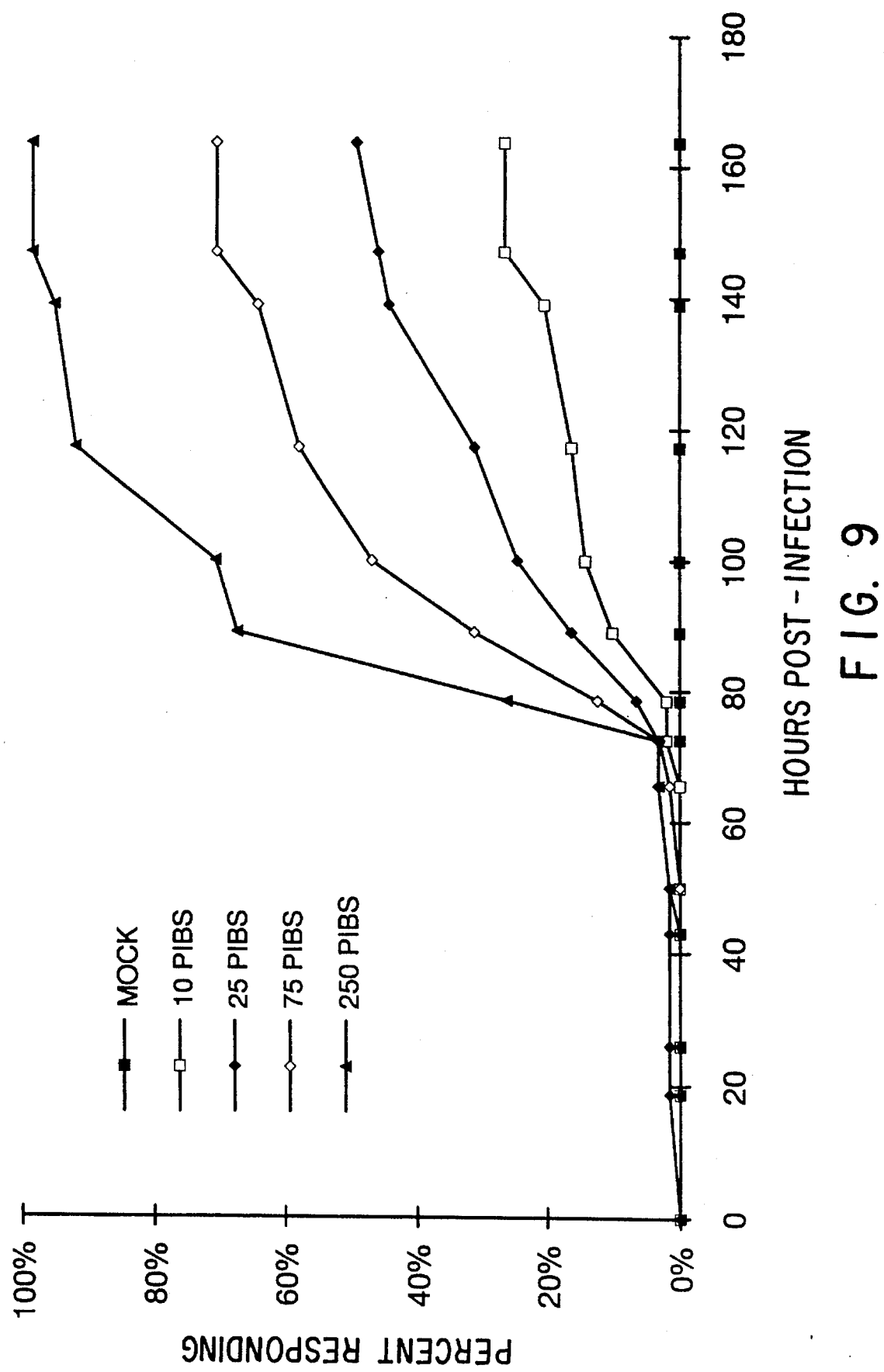
Figure 10:
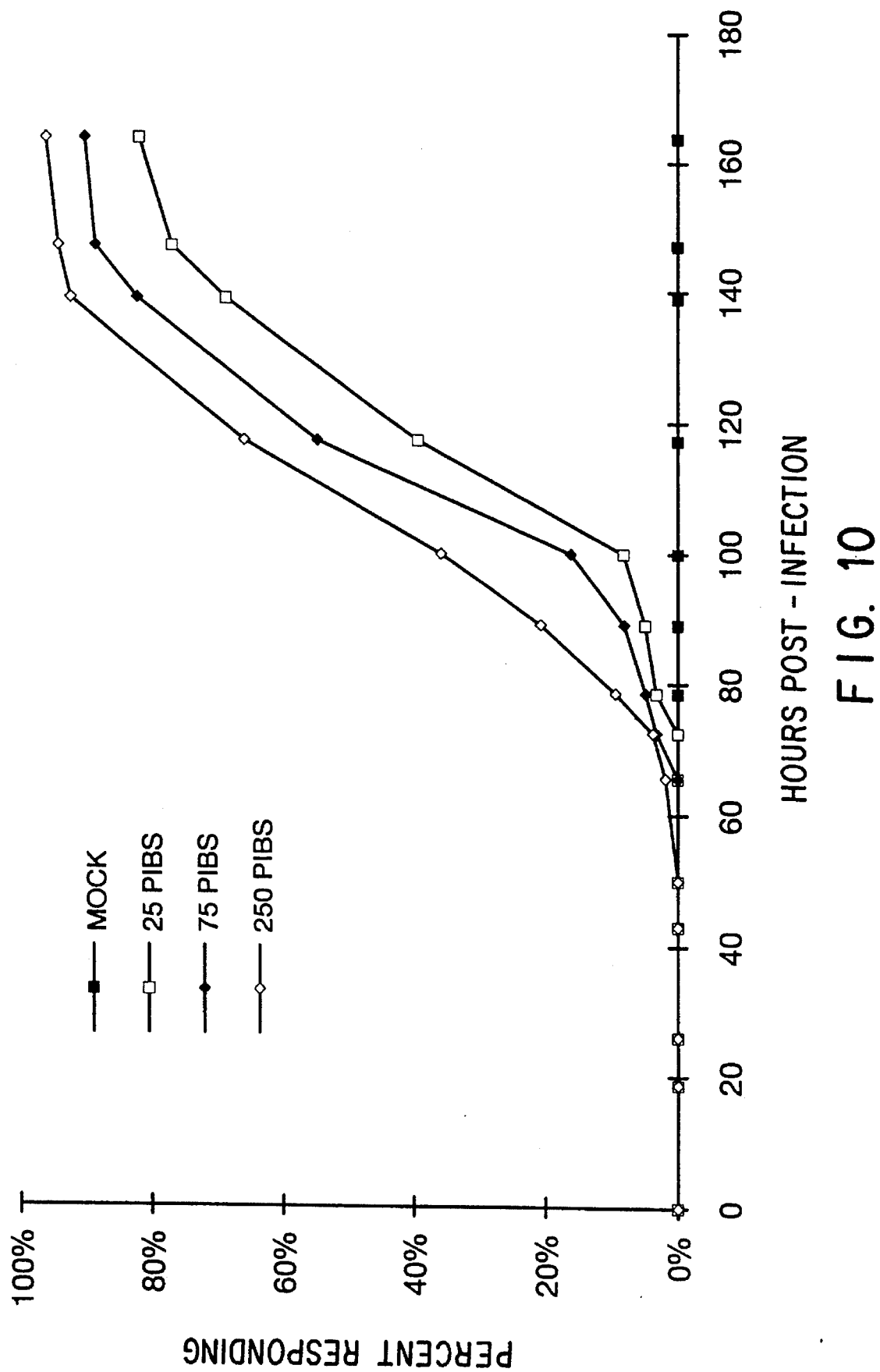
Figure 11:
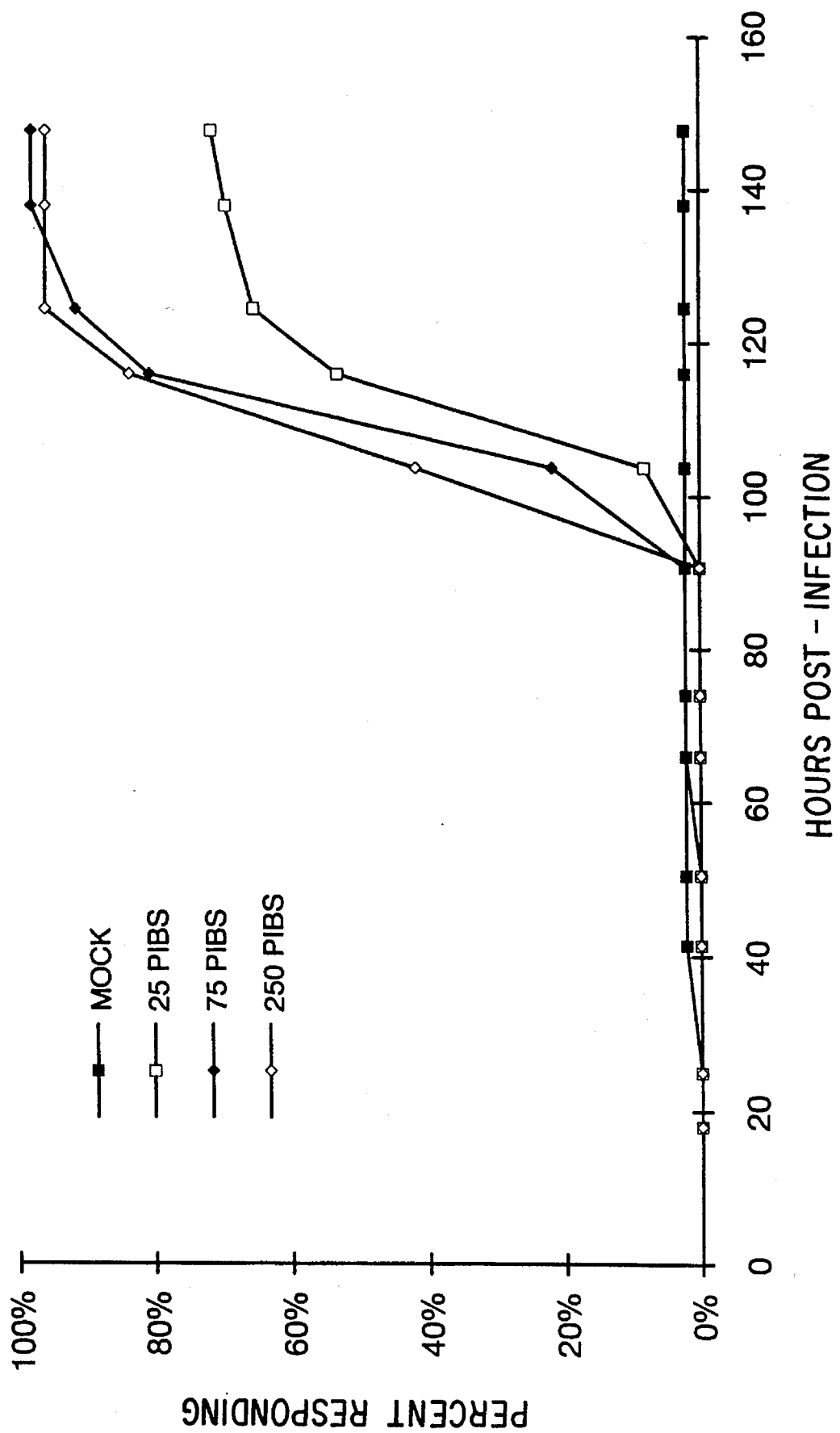
Figure 12:
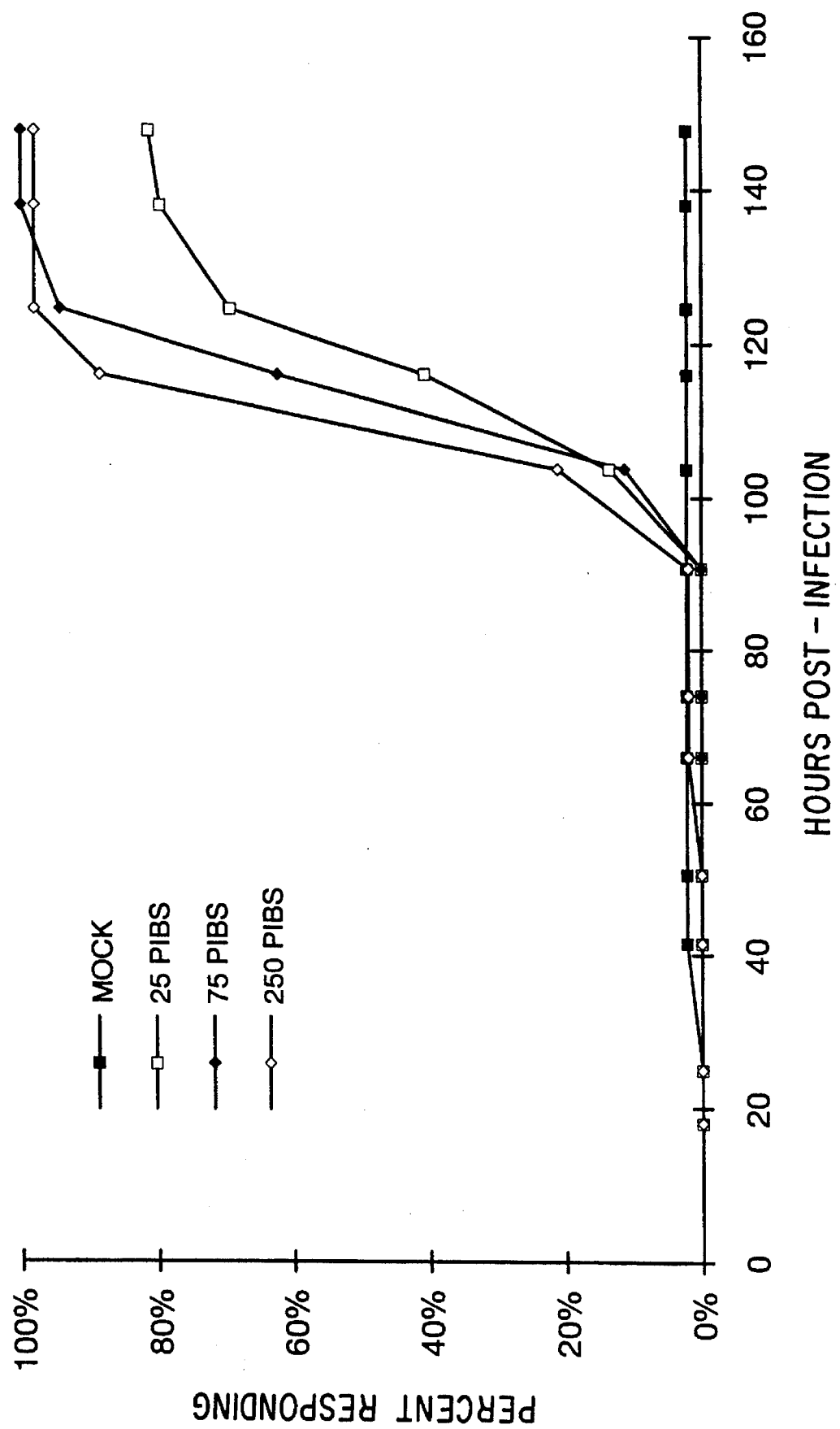
Figure 13:
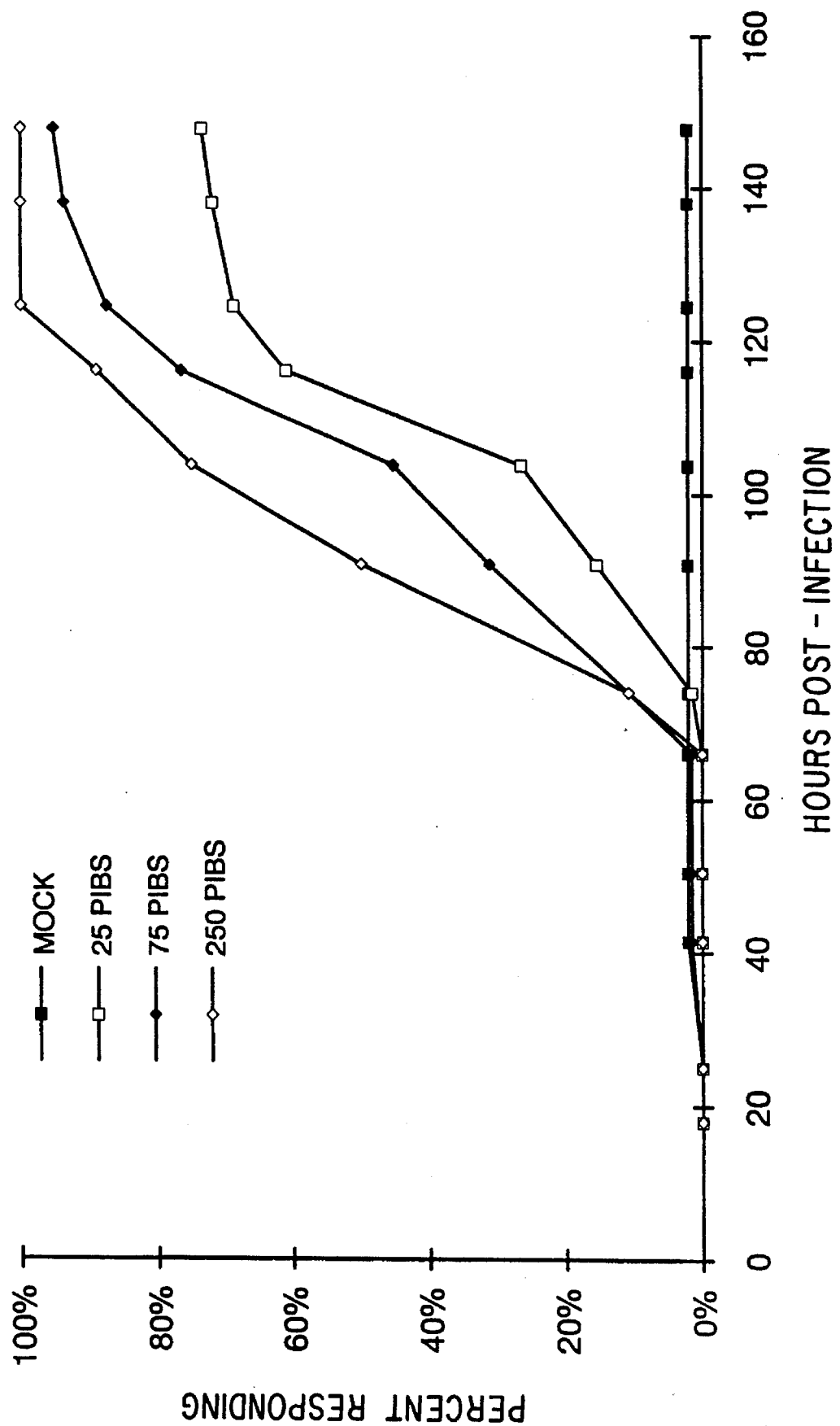
Figure 14:
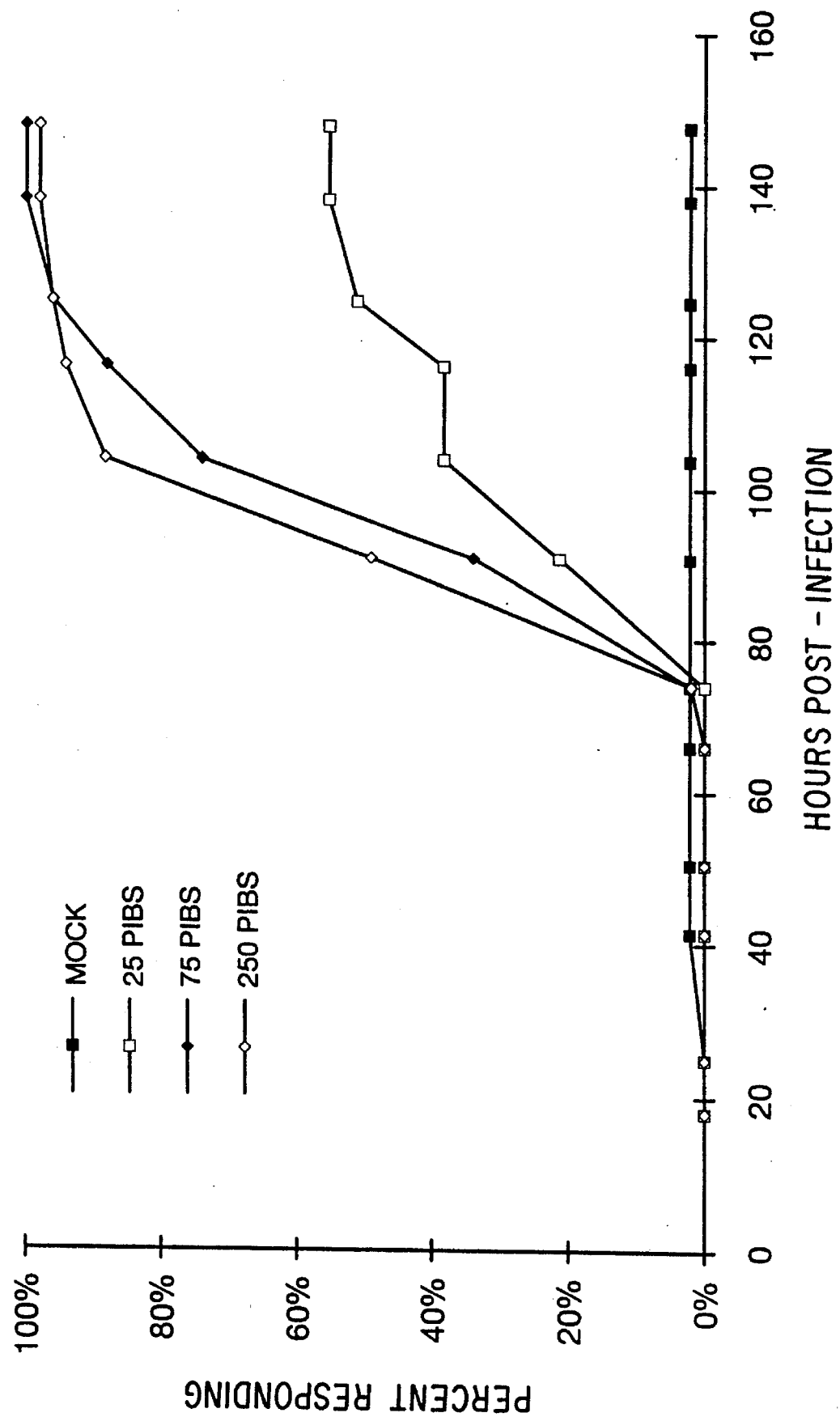
Figure 15:
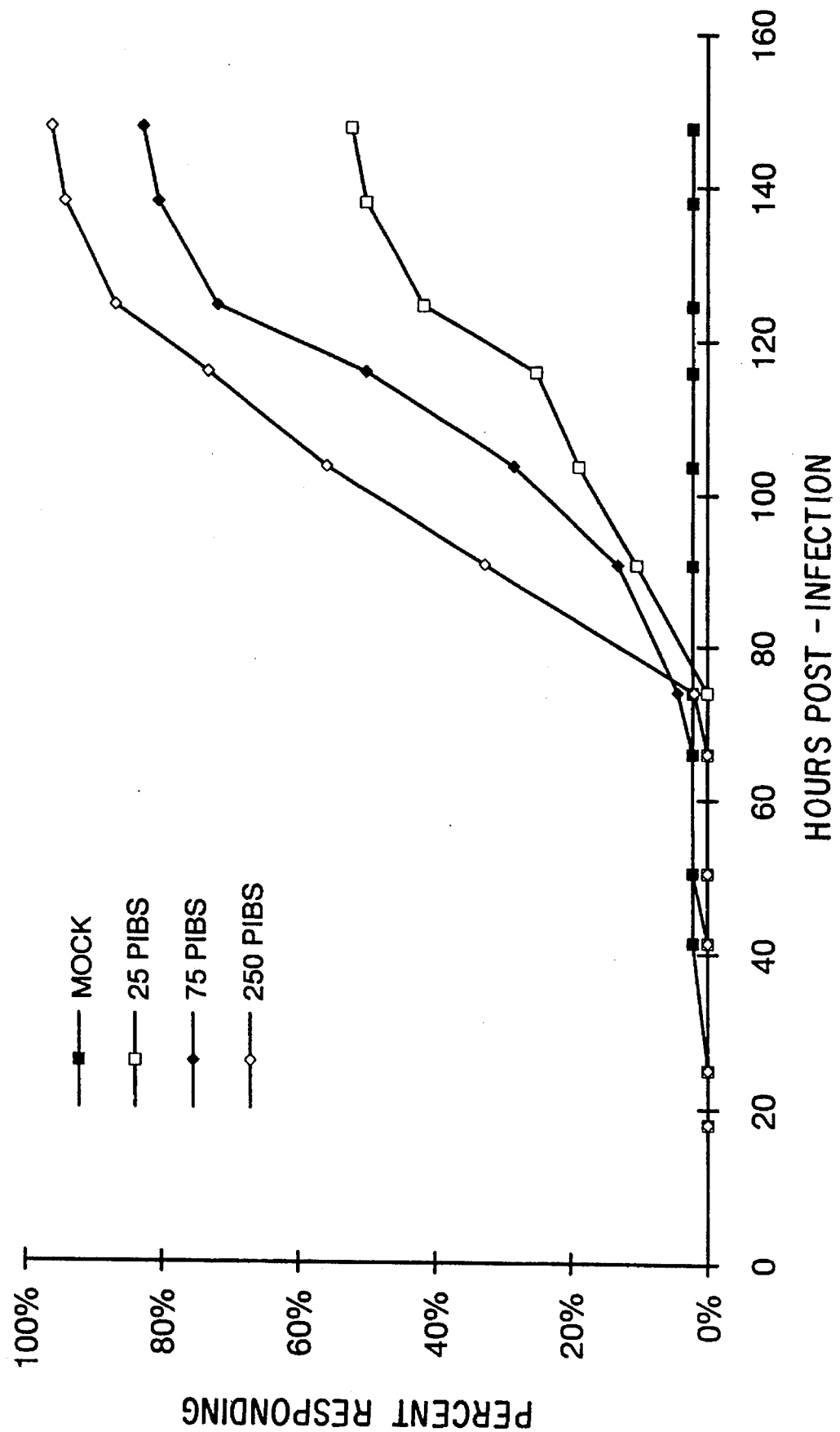

FIG. 5 summarizes the results obtained when *H. virescens* larvae are injected with $10^2$, $10^3$ and $10^4$ PFU of each virus. Forty-eight larvae are used for each virus dose. Eighty insects ("No Virus") are injected with TNM-FH alone as a negative control. The results show that the Cuticle-AaIT AcMNPV kills its host faster than the wild-type AcMNPV at each of the doses tested. At $10^4$ PFU, the $LT_{50}$ for the wild-type virus is approximately 97 hours, whereas the corresponding $LT_{50}$ for the Cuticle-AaIT AcMNPV is 67 hours. Moreover, virtually all responding larvae infected with Cuticle-AaIT, but not those infected with the wild-type AcMNPV, suffer from contractile paralysis prior to death. This result shows that insertion of the AaIT gene and the cuticle signal sequence into AcMNPV accelerates the speed of kill through the expression of biologically active toxin.

EXAMPLE 11

Further Analysis of Virus Performance by Injection into Larvae

The procedure of Example 10 is repeated by injecting separate groups of early fifth instar *Heliothis virescens* larvae with $10^4$ PFU of budded virus prepared from either the wild-type E2 strain of AcMNPV without the AaIT gene, a native AaIT signal-native AaIT gene-AcMNPV construct, or one of seven different codon optimized heterologous signal-AaIT-AcMNPV constructs. A given virus is administered to 32 larvae. Three separate assays are conducted. Larvae damaged by reason of the injection are not included in the analysis. The data are pooled and the results are depicted in the following Table:

there would be a 95% confidence level that the $LT_{50}$ would fall within the values shown for L1 and L2.

The results show that each of the codon optimized heterologous signal-AaIT-AcMNPV constructs (as well as the native AaIT signal-native AaIT gene-AcMNPV construct) kills its host faster than the wild-type AcMNPV. The $LT_{50}$ for the wild-type virus is approximately 126 hours, whereas the corresponding $LT_{50}$ for the seven heterologous signal-AaIT-AcMNPV constructs range from approximately 68–89 hours, and the native AaIT-AcMNPV construct has an $LT_{50}$ of approximately 74 hours. These results confirm the results of Example 10 that insertion of the AaIT gene and a heterologous signal sequence into AcMNPV accelerates the speed of kill through the expression of biologically active toxin.

EXAMPLE 12

Co-Occlusion of Wild-Type and Occlusion-Negative Recombinant Viruses In Viral Polyhedra Because the recombinant AaIT-viruses are defective for the production of polyhedrin, polyhedra containing a mixture of wild-type and recombinant virions are prepared by co-infecting Sf9 cells with the recombinant AaIT-virus and a wild-type helper virus (i.e., the E2 strain of AcMNPV). To determine the amount of each virus to use for co-infection, $2\times10^7$ Sf9 cells are seeded in a 150 cm² flask and infected with various amounts of the wild-type and recombinant viruses, each at a multiplicity of infection (MOI) of at least 1 plaque forming units (PFU) per cell. Four days later, the cells are counted and the percentage of cells with clearly discernible viral occlusions in the cell nucleus is determined by microscopic visualization. The total number of polyhedra is also determined by counting polyhedra in samples treated with 0.2% Triton X-100 and 2% (w/v) SDS. The results of one such analysis involving the co-occlusion of wild-type E2 AcMNPV and the cuticle-AaIT recombinant AcMNPV are summarized in the following Table:

| Bioassay Analysis of Recombinant AaIT-AcMNPV Isolates Injected Into 10d–11d *Heliothis virescens* larvae | | | | | | |
|---|---|---|---|---|---|---|
| Virus | Signal | n | df | L1(95%) | LT50 | L2(95%) |
| AcMNPV-E2 | N/A | 81 | 5 | 123.8 | 126.0 | 128.2 |
| AcMNPV-Es6/AaIT | Esterase-6 | 91 | 5 | 67.2 | 68.5 | 69.9 |
| AcMNPV-ADK/AaIT | Adipokinetic | 81 | 6 | 72.7 | 76.3 | 80.2 |
| AcMNPV-Cut/AaIT | Cuticle | 95 | 2 | 66.9 | 68.0 | 69.1 |
| AcMNPV-Chor/AaIT | Chorion | 89 | 7 | 77.3 | 79.0 | 80.8 |
| AcMNPV-PBM/AaIT | pBmHPC-12 | 87 | 4 | 87.9 | 89.6 | 91.5 |
| AcMNPV-Apo/AaIT | Apolipophorin III | 92 | 4 | 85.7 | 87.4 | 89.1 |
| AcMNPV-Sex/AaIT | SexSpecific | 87 | 5 | 77.2 | 78.7 | 80.1 |
| AcMNPV-AaIT/cDNA | AaH IT1 | 85 | 6 | 72.5 | 74.1 | 75.7 |

In the Table, "n" represents the total number of larvae from the three assays, "df" represents the degrees of freedom, "N/A" means not applicable and "L1(95%)" and "L2(95%)" represent the confidence limits of the data, such that if the assay was rerun with an equal number of larvae,

| Culture No. | MOI [WT:Cut-AaIT] | Total cells × $10^7$ | Percent of cells with occlusions | Total polyhedra × $10^8$ | Polyhedra per cell |
|---|---|---|---|---|---|
| 1 | 10:0 | 2.15 | 94% | 4.10 | 19.0 |
| 2 | 10:1 | 1.85 | 92% | 3.65 | 19.7 |
| 3 | 10:2 | 2.30 | 89% | 3.30 | 14.3 |
| 4 | 5:5 | 1.85 | 74% | 2.15 | 11.6 |
| 5 | 2:10 | 2.00 | 36% | 0.55 | 2.75 |
| 6 | 2:20 | 2.10 | 23% | 0.12 | 0.57 |

These results demonstrate that even when the MOI of the wild-type virus is at least 2 PFU per cell, both the percentage of cells with viral polyhedra (occlusions) and the average number of polyhedra per cell decrease significantly as the MOI of the recombinant virus is increased. To maintain a large fraction of recombinant virions per polyhedron without making unacceptable sacrifices in the yield of polyhedra, all subsequent co-occlusion experiments are done with both viruses (i.e., wild-type and occlusion-negative recombinant) at an MOI of 3 each.

EXAMPLE 13

Microdrop Bioassay to Measure the Oral Activity of Codon Optimized and Native Sequence Recombinant AaIT-Viruses Co-occluded into Polyhedra with Wild-Type AcMNPV To examine the oral toxicity of the recombinant AcMNPV containing a codon optimized or native sequence encoding AaIT, each virus (with the exception of the IL-2/AaIT recombinant, which is not assayed) is co-occluded with wild-type AcMNPV into viral polyhedra (see Example 11) and fed to second instar *Heliothis virescens* larvae using a microdrop bioassay procedure as follows. Individual second instar *Heliothis virescene* larvae are transferred into empty assay wells containing a disk of prewetted filter paper. One larva is placed per well. The larvae are then stored at 26° C., 50% relative humidity for 12 to 20 hours (overnight).

The next day, a 15 ml aliquot of Stoneville insect diet (46) is heated to boiling. Five mls of water are added to the melted diet. This mixture is reheated to boiling and promptly centrifuged at low speed. Supernatant is removed and a few drops of food dye are added to the clarified supernatant as an aid to visualize the diet. The molten diet is aliquoted into microfuge tubes, respun in a Beckman microfuge, and the clarified supernatant is transferred into new microfuge tubes. This molten diet is placed in a heat block at 54° C. until needed.

After the diet cools to 54° C., the desired amount of PIBs is added. Typically, this ranges from 10 to 250 PIBs per μl. After mixing well, 1 μl drops of treated diet are aliquoted onto PARAFILM™ (American National Can, Greenwich, Conn.), where they harden. The hardened drops are quickly transferred to the wells containing the individual larvae, one drop per larva. The larvae are allowed to feed for 2 hours and those larvae which consume the entire microdrop are placed into a new assay well containing a standard amount of untreated Stoneville diet. Larvae are then placed at 26° C., 50% relative humidity, and monitored twice daily for paralysis and death. Paralysis is determined by rolling larvae onto their backs and observing for 30 seconds. If the larva remains on its back, it is considered moribund. Moribund larvae generally die during the 24 hours following diagnosis. The duration of the test is generally 8 days.

Larvae are inspected two to three times daily and scored for evidence of morbidity and mortality. Both dead and moribund larvae are scored as responding to the treatment. FIGS. 6–15 summarize the results obtained with each of the viruses.

With one exception, all of the recombinant viruses demonstrate an earlier onset of response than the wild-type AcMNPV (which lacks the AaIT gene). The exception is the AcMNPV construct containing the pBMHPC-12 signal sequence linked to the codon optimized cDNA encoding AaIT, which performs approximately the same as the wild-type AcMNPV. The actual ratio of wild-type to recombinant virus in the polyhedra and in the infected insects is not analyzed.

BIBLIOGRAPHY

1. Tomalski, M. D., and Miller, L. K., *Nature*, 352, 82–85 (1991).
2. Federici, B. A., *In Vitro*, 28, 50A (1992).
3. Martens, J. W. M., et al., *App. & Envir. Microbiology*, 56, 2764–2770 (1990).
4. Eldridge, R., et al., *Insect Biochem.*, 21, 341–351 (1992).
5. Hammock, B. D., et al., *Nature*, 344, 458–461 (1990).
6. Luckow, V. A., and Summers, M. D., *Bio/Technology*, 6, 47–53 (1988).
7. Miller, L. K., *Ann. Rev. Microbiol.*, 42, 177–199 (1988).
8. Smith, G. E., and Summers, M. D., U.S. Pat. No. 4,745,051.
9. Granados, R. R., and Federici, B. A., *The Biology of Baculoviruses, I,* 99 (1986).
10. Summers, M. D., U.S. Pat. No. 5,155,037.
11. von Heinje, G., *Nuc. Acids Res.*, 14, 4683–4690 (1986).
12. Summers, M. D., and Smith, G. E., *A Manual Of Methods For Baculovirus Vectors And Insect Cell Culture Procedures*, pages 35, 38–42, Dept. of Entomology, Texas Agricultural Experiment Station and Texas A & M University, College Station, Tex. 77843-2475, Texas Agricultural Experiment Station Bulletin No. 1555 (1987).
13. Dee, A., et al., *Bio/Technology*, 8, 339–342 (1990).
14. Grantham, R., et al., *Nucl. Acids Res.*, 8, 49–62 (1980).
15. Grantham, R., et al., *Nucl. Acids Res.*, 9, 43–74 (1981).
16. Maroyama, T., et al., *Nucl. Acids Res.*, 14, 151–197 (1986).
17. Aota, S., et al., *Nucl. Acids Res.*, 16, 315–402 (1988).
18. Wada, K., et al., *Nucl. Acids Res.*, 19 Supp., 1981–1985 (1991).
19. Kurland, C. G., *FEBS Letters*, 285, 165–169 (1991).
20. Pedersen, S., *EMBO J.*, 3, 2895–2898 (1984).
21. Sorensen, M. A., *J. Mol. Biol.*, 207, 365–377 (1989).
22. Randall, L. L., et al., *Eur. J. Biochem.*, 107, 375–379 (1980).
23. Curran, J. F., and Yarus, M., *J. Mol. Biol.*, 209, 65–77 (1989).
24. Varenne, S., et al., *J. Mol. Biol.*, 180, 549–576 (1984).
25. Garel, J.-P., *J. Theor. Biol.*, 43, 211–225 (1974).
26. Ikemura, T., *J. Mol. Biol.*, 146, 1–21 (1981).
27. Ikemura, T., *J. Mol. Biol.*, 151, 389–409 (1981).

28. Ikemura, T., Mol. *Biol. Evol.*, 2, 13–24 (1985).

29. Tomalski, M. D., and Miller, L. K., *Nature*, 352, 82–85 (1991).

30. Martens, J. W. M., et al., *App. & Envir. Microbiology*, 56, 2764–2770 (1990).

31. Federici, B. A., *In Vitro*, 28, 50A (1992).

32. Menn, J. J., and Borkovec, A. B., *J. Agric. Food Chem.*, 37, 271–278 (1989).

33. Smith, G. E., and Summers, M. D., *J. Virol.*, 33, 311–319 (1980).

34. Smith, G. E., and Summers, M. D., *Virology*, 89, 519–527 (1978).

35. Luckow, V. A., and Summers, M. D., *Virology*, 170, 31–39 (1989).

36. Sambrook, J., et al., *Molecular Cloning: A Laboratory Manual*, 2nd ed., Cold Spring Harbor Laboratory Press, Cold Spring Harbor, N.Y. (1989).

37. Hooft van Iddekinge, B. J. L., et al., *Virology*, 131, 561–565 (1983).

38. Kuzio, J., et al., *Virology*, 139, 414–418 (1984).

39. Webb, N. R., and Summers, M. D., *J. Methods Cell & Molec. Biol.*, 2, 173–188 (1990).

40. Grace, T. C. C., *Nature*, 195, 788–789 (1962).

41. Malitschek, B., and Schartl, M., *BioTechniques*, 11, 177–178 (1991).

42. Glisin, V., et al., *Biochemistry*, 13, 2633–2638 (1974).

43. Chirgwin, J., et al., *Biochemistry*, 18, 5294–5299 (1979).

44. Feinberg, A. P., and Vogelstein, B., *Anal. Biochem.*, 132, 6–13 (1983).

45. Zlotkin, E., et al., *Toxicon*, 9, 1–8 (1971).

46. King, E. G., and Hartley, G. G., "*Heliothis virescens*", in *Handbook of Insect Rearing Vol. II*, Singh, P., and Moore, R. F., eds., pages 323–328 (Elsevier 1985).

---

What is claimed is:

1. An isolated nucleic acid sequence encoding a protein selected from the group consisting of the toxin from the mite species *Pyemotes tritici*, the *Bacillus thuringiensis* subsp. aizawai toxin, the *Bacillus thuringiensis* CryIVD toxin, the *Androctonus australis* insect toxin (AaIT), eclosion hormone, prothoracicotropic hormone, adipokinetic hormone, diuretic hormone, proctolin and juvenile hormone esterase, wherein immediately upstream of said sequence is a nucleic acid sequence encoding a signal sequence selected from the group consisting of the cuticle signal sequence from *Drosophila melanogaster* depicted in SEQ ID NO. 17, the chorion signal sequence from *Bombyx mori* depicted in SEQ ID NO. 13, the apolipophorin signal sequence from *Manduca sexta* depicted in SEQ ID NO. 9, the sex specific signal sequence from *Bombyx mori* depicted in SEQ ID NO. 25, the adipokinetic hormone signal sequence from *Manduca sexta* depicted in SEQ ID NO. 5, the pBMHPC-12 signal sequence from *Bombyx mori* depicted in SEQ ID NO. 1 and the esterase-6 signal sequence from *Drosophila melanogaster* depicted in SEQ ID NO. 21.

2. The sequence of claim 1 wherein the toxin is AaIT.

3. The sequence of claim 2 wherein the nucleic acid sequence encoding AaIT encodes a toxin whose amino acid sequence is depicted in SEQ ID NO. 30.

4. The sequence of claim 3 wherein the nucleic acid sequence encoding AaIT is the native nucleic acid sequence for AaIT depicted in SEQ ID NO. 29.

5. The sequence of claim 3 wherein the nucleic acid sequence encoding AaIT is a nucleic acid sequence codon optimized for Drosophila, and depicted in SEQ ID NO. 31.

6. An expression vector which contains the nucleic acid sequence of claim 1.

7. The expression vector of claim 6 wherein the expression vector is an insect virus.

8. The expression vector of claim 7 wherein the insect virus is selected from the group consisting of nuclear polyhedrosis viruses, granulosis viruses, non-occluded viruses and entomopox viruses.

9. The expression vector of claim 8 wherein the insect virus is a nuclear polyhedrosis virus selected from the group consisting of *Lymantria dispar* NPV (gypsy moth NPV), *Autographa californica* MNPV, *Syngrapha falcifera* NPV (celery looper NPV), *Spodoptera litturalis* NPV, *Spodoptera frugiperda* NPV, *Heliothis armigera* NPV, *Mamestra brassicae* NPV, *Choristoneura fumiferana* NPV, *Trichoplusia ni* NPV and *Heliocoverpa zea* NPV.

10. The expression vector of claim 8 wherein the insect virus is a granulosis virus selected from the group consisting of *Cydia pomonella* GV (coddling moth GV), *Pieris brassicae* GV and *Trichoplusia ni* GV.

11. The expression vector of claim 8 wherein the insect virus is a non-occluded virus selected from the group consisting of *Orcytes rhinoceros* NOV and *Heliothis zea* NOV.

12. The expression vector of claim 8 wherein the insect virus is an entomopox virus selected from the group consisting of *Melolontha melonotha* EPV, *Amsacta moorei* EPV, *Locusta migratoria* EPV, *Melanoplus sanguinipes* EPV, *Schistocerca gregaria* EPV, *Aedes aegypti* EPV and *Chironomus luridus* EPV.

13. The expression vector of claim 9 wherein the nuclear polyhedrosis virus is *Autographa californica* MNPV.

14. A expression vector which comprises the nucleic acid sequence of claim 1 inserted into a baculovirus transfer vector.

15. The expression vector of claim 14 wherein the baculovirus transfer vector is derived from *Autographa californica* nuclear polyhedrosis virus.

16. The expression vector of claim 15 wherein the baculovirus transfer vector is pVL985.

17. An insect host cell transformed with the nucleic acid sequence of claim 1.

18. The host cell of claim 17 wherein the insect cell is the cell line designated *Spodoptera frugiperda* 9 (Sf9).

19. A method of producing AaIT which comprises transforming or infecting an insect host cell with the nucleic acid sequence of claim 2, culturing the host cell under conditions which permit expression of said nucleic acid sequence by the host cell and isolating from the host cell the AaIT so expressed.

20. The method of claim 19 in which the insect cell is an Sf9 cell.

21. The method of claim 20 in which transformation is achieved by an expression vector.

* * * * *

UNITED STATES PATENT AND TRADEMARK OFFICE
CERTIFICATE OF CORRECTION

PATENT NO. : 5,547,871
DATED : Aug. 20, 1996
INVENTOR(S) : Bruce C. Black

It is certified that error appears in the above-indentified patent and that said Letters Patent is hereby corrected as shown below:

At the cover page, item [75] should read as follows:

[75] Inventor: Bruce C. Black, Yardley, Pa.

Signed and Sealed this

Twenty-fourth Day of June, 1997

*Attest:*

BRUCE LEHMAN

*Attesting Officer*  *Commissioner of Patents and Trademarks*